United States Patent
Oliphant et al.

(10) Patent No.: US 10,954,566 B2
(45) Date of Patent: *Mar. 23, 2021

(54) LIGATION-BASED DETECTION OF GENETIC VARIANTS

(71) Applicant: Ariosa Diagnostics, Inc., San Jose, CA (US)

(72) Inventors: Arnold Oliphant, San Jose, CA (US); Andrew Sparks, San Jose, CA (US); John Stuelpnagel, San Jose, CA (US); Ken Song, San Jose, CA (US)

(73) Assignee: Ariosa Diagnostics, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/255,064

(22) Filed: Jan. 23, 2019

(65) Prior Publication Data
US 2020/0109450 A1   Apr. 9, 2020

Related U.S. Application Data

(63) Continuation of application No. 14/880,093, filed on Oct. 9, 2015, now Pat. No. 10,233,496, which is a continuation of application No. 13/840,383, filed on Mar. 15, 2013, now abandoned, which is a continuation-in-part of application No. 13/293,419, filed on Nov. 10, 2011, now Pat. No. 10,131,937, which is a continuation-in-part of application No. 13/205,603, filed on Aug. 8, 2011, now Pat. No. (Continued)

(51) Int. Cl.
*C12Q 1/6883* (2018.01)
*C12Q 1/6862* (2018.01)
*C12Q 1/6809* (2018.01)
*C12Q 1/6827* (2018.01)

(52) U.S. Cl.
CPC ......... *C12Q 1/6883* (2013.01); *C12Q 1/6809* (2013.01); *C12Q 1/6827* (2013.01); *C12Q 1/6862* (2013.01); *C12Q 2600/156* (2013.01); *C12Q 2600/16* (2013.01)

(58) Field of Classification Search
CPC .. C12Q 1/6883; C12Q 1/6862; C12Q 1/6809; C12Q 1/6827; C12Q 2600/156; C12Q 2600/16
See application file for complete search history.

(56) References Cited

U.S. PATENT DOCUMENTS

2008/0090239 A1* 4/2008 Shoemaker ............ G01N 1/405
435/6.12

OTHER PUBLICATIONS

Porreca et al. Nature Methods. 2007. 4(11):931-36. (Year: 2007).*
(Continued)

*Primary Examiner* — Joseph G. Dauner
(74) *Attorney, Agent, or Firm* — Jennifer Rosenfield; Mintz Levin

(57) ABSTRACT

The present invention provides assays systems and methods for detection of genetic variants in a sample, including copy number variation and single nucleotide polymorphisms. The invention preferably employs the technique of tandem ligation—, e.g., the ligation of two or more fixed sequence oligonucleotides and one or more bridging oligonucleotides complementary to a region between the fixed sequence oligonucleotides—combined with detection of levels of particular genomic regions using array hybridization.

16 Claims, 15 Drawing Sheets

Specification includes a Sequence Listing.

Related U.S. Application Data 10,308,981, which is a continuation-in-part of application No. 13/013,732, filed on Jan. 25, 2011, now abandoned.

(60) Provisional application No. 61/371,605, filed on Aug. 6, 2010.

(56) References Cited

OTHER PUBLICATIONS

Tewhey et al. Nature Biotechnology. 2009. 27(11):1025-1031. (Year: 2009).*
Boyle et al. Bioinformatics. 2014. 30(18):2670-2672. (Year: 2014).*
Myllykangas et al. Biotechnol Genet Eng Rev. 2010. 27:135-158. (Year: 2010).*
Turner et al. Nat. Methods. 2009. 6(5):315-316. (Year: 2009).*

* cited by examiner

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Universal PCR Priming Sequence

<400> SEQUENCE: 1
tacaccggcg ttatgcgtcg agac                                        24

```
<210> SEQ ID NO 2
<211> LENGTH: 24
<212> TYPE: DNA
<213> ORGANISM: Artificial Sequence
<220> FEATURE:
<223> OTHER INFORMATION: Universal PCR Priming Sequence

<400> SEQUENCE: 2
attgcgggga ccgatgatcg cgtc                                              24

<210> SEQ ID NO 3
<211> LENGTH: 48
<212> TYPE: DNA
<213> ORGANISM: Artificial Sequence
<220> FEATURE:
<223> OTHER INFORMATION: Universal PCR Priming Sequence

<400> SEQUENCE: 3
taatgatacg gcgaccaccg agatctacac cggcgttatg cgtcgaga                    48

<210> SEQ ID NO 4
<211> LENGTH: 56
<212> TYPE: DNA
<213> ORGANISM: Artificial Sequence
<220> FEATURE:
<223> OTHER INFORMATION: Universal PCR Priming Sequence
<220> FEATURE:
<221> NAME/KEY: n
<222> LOCATION: (26)..(29)
<223> OTHER INFORMATION: n = a, t, c or g
<220> FEATURE:
<221> NAME/KEY: misc_feature
<222> LOCATION: (26)..(29)
<223> OTHER INFORMATION: n is a, c, g, or t

<400> SEQUENCE: 4
tcaagcagaa gacggcatac gagatnnnna aacgacgcga tcatcggtcc ccgcaa           56
```

LIGATION-BASED DETECTION OF GENETIC VARIANTS

CROSS-REFERENCE TO RELATED APPLICATIONS

The present application is a continuation of U.S. Ser. No. 14/880,093, filed Oct. 9, 2015, which is a continuation of U.S. Ser. No. 13/840,383, filed 15 Mar. 2013; which is a continuation-in-part of U.S. Ser. No. 13/293,419, filed 10 Nov. 2011; which is a continuation-in-part of U.S. Ser. No. 13/205,603, filed 8 Aug. 2011 which is a continuation-in-part of U.S. Ser. No. 13/013,732, filed 25 Jan. 2011; which claims priority to U.S. Ser. No. 61/371,605, filed 6 Aug. 2010. The disclosures of the above-referenced applications are herein expressly incorporated by reference in their entireties.

FIELD OF THE INVENTION

This invention relates to multiplexed selection, amplification, and detection of targeted regions from a genetic sample.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genetic abnormalities account for a wide number of pathologies, including pathologies caused by chromosomal aneuploidy (e.g., Down's syndrome), germline mutations in specific genes (e.g., sickle cell anemia), and pathologies caused by somatic mutations (e.g., cancer). Diagnostic methods for determining such genetic anomalies have become standard techniques for identifying specific diseases and disorders, as well as providing valuable information on disease source and treatment options.

Copy-number variations are alterations of genomic DNA that correspond to relatively large regions of the genome that have been deleted or amplified on certain chromosomes. CNVs can be caused by genomic rearrangements such as deletions, duplications, inversions, and translocations. Copy number variation has been associated with various forms of cancer (Cappuzzo F, Hirsch, et al. (2005) 97 (9): 643-655) neurological disorders (Sebat, J., et al. (2007) *Science* 316 (5823): 445-9, including autism (Sebat, J., et al. (2007) *Science* 316 (5823): 445-9), and schizophrenia St Clair D (2008). *Schizophr Bull* 35 (1): 9-12. Detection of copy number variants of a chromosome of interest or a portion thereof in a specific cell population can be a powerful tool to identify genetic diagnostic or prognostic indicators of a disease or disorder.

Detection of copy number variation is also useful in detecting chromosomal aneuploidies in fetal DNA. Conventional methods of prenatal diagnostic testing currently requires removal of a sample of fetal cells directly from the uterus for genetic analysis, using either chorionic villus sampling (CVS) between 11 and 14 weeks gestation or amniocentesis after 15 weeks. However, these invasive procedures carry a risk of miscarriage of around 1% Mujezinovic and Alfirevic, Obstet Gynecol 2007; 110:687-694. A reliable and convenient method for non-invasive prenatal diagnosis has long been sought to reduce this risk of miscarriage and allow earlier testing.

Single nucleotide polymorphisms (SNPs) are single nucleotide differences at specific regions of the genome. The average human genome typically has more than three million SNPs when compared to a reference genome. SNPs have been associated with various diseases, including cancer, cardiovascular disease, cystic fibrosis, and diabetes. Detection of SNPs can be a powerful tool to identify genetic diagnostic or prognostic indicators of a disease or disorder. It is often desirable to detect many different SNPs in the same sample.

Re-sequencing is the use of DNA sequence detection, often in a portion of the genome. Re-sequencing can be applied towards the analysis of a genetic sample from any source including mammals, other animal species, plants, bacteria, viruses, and the like. Re-sequencing can be used for many applications including but not limited to clinical applications and environmental applications. One use of re-sequencing for clinical applications is the determination of the DNA sequence in a disease causing gene. Examples of gene re-sequencing for medical diagnostic or prognostic indications include the re-sequencing of BRCA1 and BRCA2 for breast cancer risk. An example of an environmental application would be the detection of a specific pathogen in a water source.

There is thus a need for methods of screening for copy number variations, SNPs and re-sequencing that employs an efficient, reproducible multiplexed assay. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides assays systems and methods for detection of copy number variation, polymorphisms, mutations and re-sequencing. The invention employs the technique of selecting genomic regions using fixed sequence oligonucleotides and joining them via ligation and/or extension. In a preferred aspect this is accomplished by tandem ligation, i.e. the ligation of two or more non-adjacent, fixed sequence oligonucleotides and a bridging oligonucleotide that is complementary to a region between and directly adjacent to the portion of the nucleic acid region of interest complementary to the fixed sequence oligonucleotides.

In one general aspect, the invention provides an assay system for detecting a nucleic acid region of interest in a genetic sample, comprising the steps of providing a genetic sample; introducing a first and second fixed sequence oligonucleotide to the genetic sample under conditions that allow the fixed sequence oligonucleotides to specifically hybridize to complementary regions in the nucleic acid of interest; introducing one or more bridging oligonucleotides under conditions that allow the fixed sequence oligonucleotides to specifically hybridize to complementary regions in the nucleic acid of interest, wherein the one or more bridging oligonucleotides are complementary to a region of the nucleic acid between and immediately adjacent to the region complementary to the first and second fixed sequence oligonucleotides; ligating the hybridized oligonucleotides to create a contiguous ligation product complementary to the nucleic acid region of interest; amplifying the contiguous ligation product to create amplification products having the sequence of the nucleic acid region; and detecting and quantifying the amplification products, wherein detection of the amplification product provides detection of the nucleic acid region in the genetic sample. The amplification products are optionally isolated and quantified to determine the relative frequency of the nucleic acid region in the genetic sample.

In another general aspect, the invention provides an assay system for detecting a nucleic acid region of interest in a genetic sample, comprising the steps of providing a genetic sample; introducing a first and second fixed sequence oligonucleotide to the genetic sample under conditions that allow the fixed sequence oligonucleotides to specifically hybridize to complementary regions in the nucleic acid of interest; introducing one or more bridging oligonucleotides complementary to a region of the nucleic acid of interest between the regions complementary to the first and second fixed sequence oligonucleotides under conditions that allow the bridging oligonucleotides to specifically hybridize to the nucleic acid of interest, wherein at least one or more bases on either or both ends of the bridging oligonucleotide are not immediately adjacent to the fixed sequence oligonucleotides; extending the one or more bridging oligonucleotides so that the bridging oligonucleotides are immediately adjacent to the fixed sequence oligonucleotides; ligating the hybridized and extended oligonucleotides to create a contiguous ligation product; amplifying the contiguous ligation product to create amplification products having the sequence of the nucleic acid region of interest; and detecting and quantifying the amplification products, wherein detection of the amplification product provides detection of the nucleic acid region in the genetic sample. The amplification products are optionally isolated and quantified to determine the relative frequency of the nucleic acid region in the genetic sample.

The relative frequency of the nucleic acid in the sample can be used to determine not only copy number variation for that particular nucleic acid region, but also in conjunction with and/or in comparison to other nucleic acids, it may be used to determine the copy number variation of larger genomic regions, including chromosomes.

The fixed sequence oligonucleotides used in the assay system preferably comprise universal primer regions that are used in amplification of the contiguous ligation product. Alternatively, the universal primer sequences can be added to the contiguous ligation products following the ligation of the hybridized fixes sequence and bridging oligonucleotides, e.g., through the introduction of adapters comprising such universal primer sequences to the ends of the contiguous ligation product.

The bridging oligonucleotides are preferably shorter oligonucleotides, preferably between 1-10 nucleotides and more preferably between 3-7 nucleotides, and can be designed to provide degeneracy within the sequence of the bridging oligonucleotides, e.g., the bridging oligonucleotides are provided as full or partial randomers with various sequence variations to ensure detection of the selected nucleic region even if the region contains a polymorphic reside. The degeneracy of the bridging oligonucleotide can be determined based on the predicted polymorphisms that may be present in the selected nucleic acid region. Alternatively, the pool of bridging oligonucleotides used in a reaction can provide degeneracy for one or more position of the bridging oligonucleotide. In one aspect, the pool of bridging oligonucleotides used in a reaction can provide degeneracy for each position of the bridging oligonucleotide. In yet another aspect, the pool of bridging molecules used in a reaction can provide degeneracy for each internal position of the bridging oligonucleotide, with the nucleotides adjacent to the ligation sites remaining constant in the pool of bridging oligonucleotides used within the set. In another aspect, the bridging oligo is longer than 10 nucleotides and preferably 18-30 nucleotides. In a preferred aspect, a single bridging oligonucleotide complementary to a region of the nucleic acid of interest is hybridized between the region complementary to the first and second fixed sequence oligonucleotides. In another aspect, two or more bridging oligonucleotides are hybridized within the region between the fixed sequence oligonucleotides, and preferably the bridging oligonucleotides hybridize to adjacent regions on the nucleic acid of interest. In this situation, ligation occurs between the fixed sequence oligonucleotides and the adjacent bridging oligonucleotides as well as between adjacent bridging oligonucleotides. In another aspect, there are one or more bases between the serial bridging oligonucleotides and/or one or more bases between the bridging oligonucleotides and fixed sequence oligonucleotides. These gaps can be extended, e.g., by use of polymerase and dNTPs prior to ligation.

It is an advantage that using degenerate bridging oligonucleotides obviates the need to predetermine the maternal and fetal polymorphic content for a selected nucleic acid region prior to employing the detection methods of the assay system.

In one aspect of the invention, the first and second fixed sequence oligonucleotides are introduced to the genetic sample and specifically hybridized to the complementary portions of the nucleic acids of interest prior to introduction of the bridging oligonucleotides. The hybridized regions are optionally isolated following the specific hybridization of the fixed sequence oligonucleotides to remove any excess unbound oligonucleotides in the reaction.

In another aspect, the bridging oligonucleotides are introduced to the genetic sample at the same time the fixed sequence oligonucleotides are introduced, and all are allowed to hybridize to a contiguous portion of the nucleic acid region of interest.

In certain aspects, the fixed sequence oligonucleotides of the invention comprise one or more indices. These indices may serve as surrogate sequences for the identification of the nucleic acid region of interest, a locus, or a particular allele of a locus. In particular, these indices may serve as surrogate detection sequences for the detection of hybridization of the nucleic acid region of interest to an array. Other indices may be used to correspond an amplification product to a particular sample, or to identify experimental error within the assay methods. In particular assays, the amplification product from the contiguous ligation product is identified and quantified using one or more indices as a surrogate to the actual sequence of the amplification product.

In specific assay systems, the first or second fixed sequence oligonucleotide comprise an allele index that associates a specific allele with that complementary fixed sequence oligonucleotide.

In other specific aspects of the invention, the fixed sequence oligonucleotides are used for comparative hybridization of genomic regions, e.g., genomic regions corresponding to a particular locus or chromosome.

In certain aspects of the invention, an assay system employs two index sequences that allow direct comparison of levels of particular genomic regions in a sample using array hybridization.

In a general aspect of the invention, a method is provided for detecting a variance in the frequency of a genomic region in a genetic sample. This method comprises the steps of providing a maternal sample, introducing at east two sets of first and second fixed sequence oligonucleotides to specifically hybridize to complementary regions in nucleic acid regions of interest, wherein each set comprises an oligonucleotide associated with an optically detectable label, and wherein both sets comprise a region that binds selectively to a single array feature; ligating the hybridized oligonucleotides to create contiguous ligation products complementary to nucleic acid regions of interest; introducing the contiguous ligation product from both sets to an array comprising one or more features complementary to the contiguous ligation products; and detecting the hybridization of the contiguous ligation products from the first and second set by detection of the optically detectable labels; wherein the relative frequency of the optically detectable labels on the array is indicative of the presence or absence of a variance in the frequency of a nucleic acid region of interest in the genetic sample.

In another general aspect of the invention, a method is provided for detecting regions of interest corresponding to a first and second chromosome in a genetic sample. This method comprises the steps of providing a genetic sample 1 introducing at least two sets of first and second fixed sequence oligonucleotides to the genetic sample under conditions that allow the sets of fixed sequence oligonucleotides to specifically hybridize to complementary regions in nucleic acid regions of interest, wherein the first set of fixed sequence oligonucleotides is complementary to a genomic region on a first chromosome and the second set of fixed sequence oligonucleotides is complementary to a genomic region on a second chromosome, and wherein each set comprises an oligonucleotide associated with an optically detectable label, and wherein both sets comprise a region that binds selectively to a single array feature; ligating the hybridized oligonucleotides to create contiguous ligation products complementary to nucleic acid regions of interest; introducing the contiguous ligation products from both sets to an array comprising one or more features complementary to the contiguous ligation products; and detecting hybridization of the contiguous ligation products from the first and second set to the array by detection of the optically detectable labels; wherein the relative frequency of the optically detectable labels on the array is indicative of the presence or absence of a variance in the frequency of a first and second chromosome in the genetic sample.

In certain specific aspects, the method is carried out for one to 10,000 nucleic acid regions of interest on a chromosome, such as two to 1,000 nucleic acid regions of interest or any intervening range.

In certain specific aspects, hybridization of contiguous ligation products comprises hybridization to individual oligonucleotides bound to the array.

In certain aspects, variance is detected by an alteration of the expected ratio of nucleic acids of interest in the genetic sample. In certain specific aspects the variance is detected by an increased or decreased level of hybridization of one set of contiguous ligation products as compared to a second set of contiguous ligation products.

In another general aspect of the invention, an assay system is provided for detecting a nucleic acid region of interest in a maternal sample comprising both maternal and fetal cell free DNA. This assay system comprises the steps of providing a maternal sample comprising cell free DNA from both maternal and fetal sources; introducing a first and second non-adjacent, fixed sequence oligonucleotide to the genetic sample under conditions that allow the fixed sequence oligonucleotides to specifically hybridize to complementary regions in the nucleic acid of interest; introducing one or more bridging oligonucleotides under conditions that allow the bridging oligonucleotides to specifically hybridize to complementary regions in the nucleic acid of interest, wherein one or more bridging oligonucleotides are complementary to a region of the nucleic acid between and immediately adjacent to the region complementary to the first and second fixed sequence oligonucleotides; ligating the hybridized oligonucleotides to create a contiguous ligation product complementary to the nucleic acid region of interest; amplifying the contiguous ligation product to create amplification products having the sequence of the nucleic acid region; and detecting and quantifying the amplification products; wherein quantification of the amplification product provides a relative frequency of the nucleic acid region in the maternal sample.

The relative frequency of the nucleic acid in the sample can be used to determine not only copy number variation for that particular nucleic acid region, but also in conjunction with and/or in comparison to other nucleic acids, it may be used to determine the copy number variation of larger genomic regions, including chromosomal imbalance between maternal and fetal nucleic acid regions due to aneuploidy in the fetus.

The invention also provides compositions that are useful in ligation-based nucleic acid detection assays such as those of the present invention. Accordingly, the invention provides sets of oligonucleotides for ligation-based detection of a nucleic acid region of interest, comprising a first oligonucleotide that comprises sequences complementary to the sequences of a first portion of a nucleic acid region, a universal primer sequence, and optionally one or more indices; a second oligonucleotide that comprises sequences complementary to the sequence of a second portion of a nucleic acid region and a universal primer sequence; and one or more bridging oligonucleotides that are complementary to the region immediately adjacent and between the nucleic acid region complementary to the first and second oligonucleotides. In certain aspects, the set of oligonucleotides comprises two or more bridging oligonucleotides with the ability to identify different polymorphisms within the nucleic acid of interest. In other aspects, the bridging molecules provide degeneracy for each position of the bridging oligonucleotide. In yet other aspects, the bridging molecules provide degeneracy for each internal position of the bridging oligonucleotide, with the nucleotides adjacent to the ligation sites remaining constant in the pool of bridging oligonucleotides used within the set.

These aspects and other features and advantages of the invention are described in more detail below.

DEFINITIONS

Figure 1:
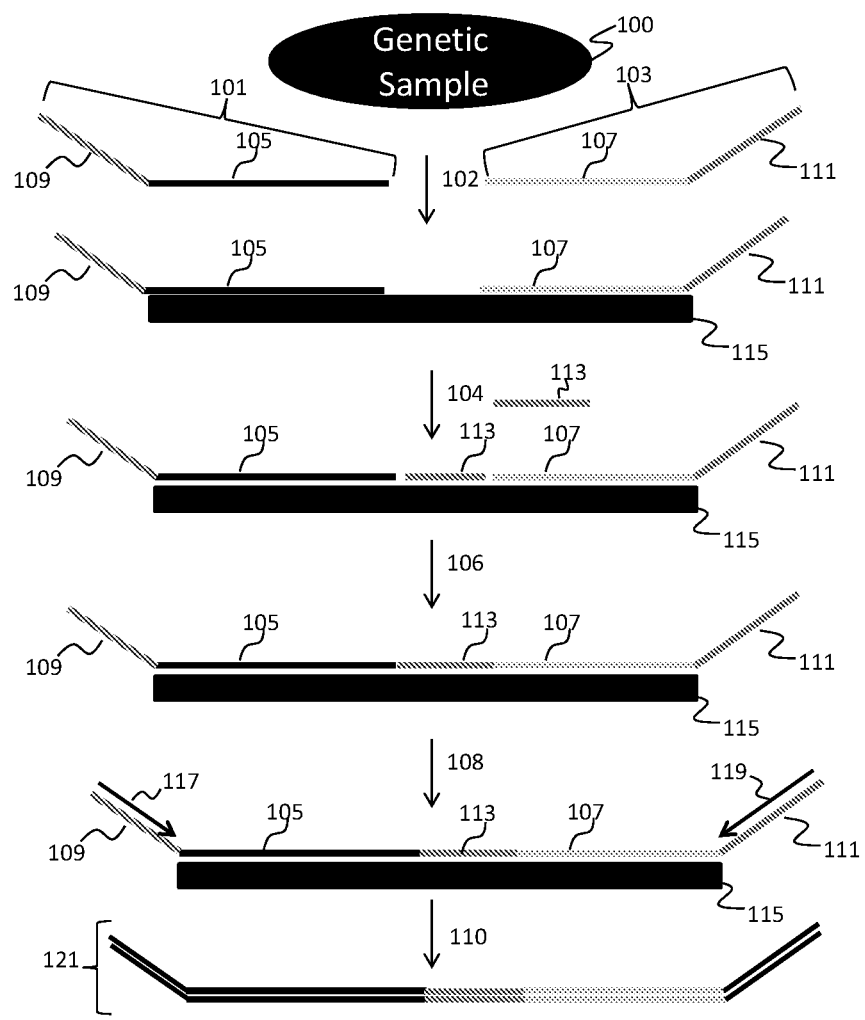
FIG. 1 illustrates a first general schematic for a ligation-based assay system of the invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "allele index" refers generally to a series of nucleotides that corresponds to a specific SNP. The allele index may contain additional nucleotides that allow for the detection of deletion, substitution, or insertion of one or more bases. The index may be combined with any other index to create one index that provides information for two properties (e.g., sample-identification index, allele-locus index).

The term "binding pair" means any two molecules that specifically bind to one another using covalent and/or non-covalent binding, and which can be used for attachment of genetic material to a substrate. Examples include, but are not limited to, ligands and their protein binding partners, e.g., biotin and avidin, biotin and streptavidin, an antibody and its particular epitope, and the like.

The term "chromosomal abnormality" refers to any genetic variant for all or part of a chromosome. The genetic variants may include but not be limited to any copy number variant such as duplications or deletions, translocations, inversions, and mutations.

The terms "complementary" or "complementarity" are used in reference to nucleic acid molecules (i.e., a sequence of nucleotides) that are related by base-pairing rules. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100% complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Stringent hybridization conditions will typically include salt concentrations of less than about 1 M, more usually less than about 500 mM and preferably less than about 200 mM. Hybridization temperatures are generally at least about 2° C. to about 6° C. lower than melting temperatures ($T_m$).

The term "correction index" refers to an index that may contain additional nucleotides that allow for identification and correction of amplification, sequencing or other experimental errors including the detection of deletion, substitution, or insertion of one or more bases during sequencing as well as nucleotide changes that may occur outside of sequencing such as oligo synthesis, amplification, and any other aspect of the assay.

The term "diagnostic tool" as used herein refers to any composition or assay of the invention used in combination as, for example, in a system in order to carry out a diagnostic test or assay on a patient sample.

The term "genetic sample" refers to any sample comprising all or a portion of the genetic information of an organism, including but not limited to virus, bacteria, fungus, plants and animals, and in particular mammals. The genetic information that can be interrogated within a genetic sample includes genomic DNA (both coding and non-coding regions), mitochondrial DNA, RNA, and nucleic acid products derived from each of these. Such nucleic acid products include cDNA created from mRNA or products of pre-amplification to increase the material for analysis.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The term "identification index" refers generally to a series of nucleotides that are incorporated into an oligonucleotide during oligonucleotide synthesis for identification purposes. Identification index sequences are preferably 6 or more nucleotides in length. In a preferred aspect, the identification index is long enough to have statistical probability of labeling each molecule with a target sequence uniquely. For example, if there are 3000 copies of a particular target sequence, there are substantially more than 3000 identification indexes such that each copy of a particular target sequence is likely to be labeled with a unique identification index. The identification index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay. The index may be combined with any other index to create one index that provides information for two properties (e.g., sample-identification index, allele-locus index).

The term "identification index" refers generally to a series of nucleotides incorporated into a primer region of an amplification process for unique identification of an amplification product of a nucleic acid region. Identification index sequences are preferably 6 or more nucleotides in length. In a preferred aspect, the identification index is long enough to have statistical probability of labeling each molecule with a target sequence uniquely. For example, if there are 3000 copies of a particular target sequence, there are substantially more than 3000 identification indexes such that each copy of a particular target sequence is likely to be labeled with a unique identification index. The identification index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay. The index may be combined with any other index to create one index that provides information for two properties (e.g., sample-identification index, locus-identification index).

As used herein the term "ligase" refers generally to a class of enzymes, DNA ligases (typically T4 DNA ligase), which can link pieces of DNA together. The pieces must have compatible ends—either with both of them blunt or with mutually-compatible sticky ends—and the reaction requires ATP. "Ligation" is the process of joining two pieces of DNA together.

The terms "locus" and "loci" as used herein refer to a nucleic acid regions of known location in a genome.

The term "locus index" refers generally to a series of nucleotides that correspond to a given genomic locus. In a preferred aspect, the locus index is long enough to label each target sequence region uniquely. For instance, if the method uses 192 target sequence regions, there are at least 192 unique locus indexes, each uniquely identifying each target region. The locus index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay. The index may be combined with any other index to create one index that provides information for two properties (e.g. sample-identification index, allele-locus index).

The term "maternal sample" as used herein refers to any sample taken from a pregnant mammal which comprises both fetal and maternal cell free DNA. Preferably, maternal samples for use in the invention are obtained through relatively non-invasive means, e.g., phlebotomy or other standard techniques for extracting peripheral samples from a subject.

The term "melting temperature" or $T_m$ is commonly defined as the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+16.6(\log 10[Na+]) 0.41(\%[G+C])-675/n-1.0$ m, when a nucleic acid is in aqueous solution having cation concentrations of 0.5 M or less, the (G+C) content is between 30% and 70%, n is the number of bases, and m is the % age of base pair mismatches (see, e.g., Sambrook J et al., *Molecular Cloning, A Laboratory Manual,* 3rd Ed., Cold Spring Harbor Laboratory Press (2001)). Other references include more sophisticated computations, which take structural as well as sequence characteristics into account for the calculation of $T_m$.

"Microarray" or "array" refers to a solid phase support having a surface, preferably but not exclusively a planar or substantially planar surface, which carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., *Microarrays: A Practical Approach*, IRL Press, Oxford (2000). "Array analysis", "analysis by array" or "analysis by microarray" refers to analysis, such as, e.g., sequence analysis, of one or more biological molecules using a microarray.

The term "oligonucleotides" or "oligos" as used herein refers to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more. Suitable nucleic acid molecules may be prepared by the phosphoramidite method described by Beaucage and Carruthers (Tetrahedron Lett., 22:1859-1862 (1981)), or by the triester method according to Matteucci, et al. (J. Am. Chem. Soc., 103:3185 (1981)), both incorporated herein by reference, or by other chemical methods such as using a commercial automated oligonucleotide synthesizer.

As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [aS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

According to the present invention, a "nucleotide" may be unlabeled or detectably labeled by well known techniques. Fluorescent labels and their attachment to oligonucleotides are described in many reviews, including Haugland, *Handbook of Fluorescent Probes and Research Chemicals,* 9th Ed., Molecular Probes, Inc., Eugene Oreg. (2002); Keller and Manak, *DNA Probes,* 2nd Ed., Stockton Press, New York (1993); Eckstein, Ed., *Oligonucleotides and Analogues: A Practical Approach*, IRL Press, Oxford (1991); Wetmur, *Critical Reviews in Biochemistry and Molecular Biology*, 26:227-259 (1991); and the like. Other methodologies applicable to the invention are disclosed in the following sample of references: Fung et al., U.S. Pat. No. 4,757, 141; Hobbs, Jr., et al., U.S. Pat. No. 5,151,507; Cruickshank, U.S. Pat. No. 5,091,519; Menchen et al., U.S. Pat. No.

5,188,934; Begot et al., U.S. Pat. No. 5,366,860; Lee et al., U.S. Pat. No. 5,847,162; Khanna et al., U.S. Pat. No. 4,318,846; Lee et al., U.S. Pat. No. 5,800,996; Lee et al., U.S. Pat. No. 5,066,580: Mathies et al., U.S. Pat. No. 5,688,648; and the like. Labeling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), CASCADE BLUE® (pyrenyloxytrisulfonic acid), OREGON GREEN™ (2',7'-difluorofluorescein), TEXAS RED™ (sulforhodamine 101 acid chloride), Cyanine and 5-(2'-aminoethyl)aminonaphthalene-1-sulfonic acid (EDANS). Specific examples of fluroescently labeled nucleotides include [R6G]dUTP, [TAMRA]dUTP, [R110] dCTP, [R6G]dCTP, [TAMRA] dCTP, [JOE] ddATP, [R6G]ddATP, [FAM]ddCTP, [R110] ddCTP, [TAMRA]ddGTP, [ROX] ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink FluorX-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosomee Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, CASCADE BLUE®-7-UTP (pyrenyloxytrisulfonic acid-7-UTP), CASCADE BLUE®-7-dUTP (pyrenyloxytrisulfonic acid-7-dUTP), fluorescein-12-UTP, fluorescein-12-dUTP, OREGON GREEN™ 488-5-dUTP (2',7'-difluorofluorescein-5-dUTP), RHODAMINE GREEN™-5-UTP ((5-{2-[4-(aminomethyl)phenyl]-5-(pyridin-4-yl)-1H-i-5-UTP)), RHODAMINE GREEN™-5-dUTP ((5-{2-[4-(aminomethyl)phenyl]-5-(pyridin-4-yl)-1H-i-5-dUTP)), tetramethylrhodamine-6-UTP, tetramethylrhodamine-6-dUTP, TEXAS RED™-5-UTP (sulforhodamine 101 acid chloride-5-UTP), TEXAS RED™-5-dUTP (sulforhodamine 101 acid chloride-5-dUTP), and TEXAS RED™-12-dUTP (sulforhodamine 101 acid chloride-12-dUTP) available from Molecular Probes, Eugene, Oreg.

As used herein the term "polymerase" refers to an enzyme that links individual nucleotides together into a long strand, using another strand as a template. There are two general types of polymerase—DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification methods may be used as an alternative to PCR.

The term "polymorphism" as used herein refers to any genetic changes or variants in a loci that may be indicative of that particular loci, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a nucleic acid region to a capture oligonucleoitide for detection of a specific nucleic acid region.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The terms "sequencing" as used herein refers generally to any and all biochemical methods that may be used to determine the order of nucleotide bases including but not limited to adenine, guanine, cytosine and thymine, in one or more molecules of DNA. As used herein the term "sequence determination" means using any method of sequencing known in the art to determine the sequence nucleotide bases in a nucleic acid.

The term "sample index" refers generally to a series of unique nucleotides (i.e., each sample index is unique), and can be used to allow for multiplexing of samples in a single reaction vessel such that each sample can be identified based on its sample index. In a preferred aspect, there is a unique sample index for each sample in a set of samples, and the samples are pooled during sequencing. For example, if twelve samples are pooled into a single sequencing reaction, there are at least twelve unique sample indexes such that each sample is labeled uniquely. The sample index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay. The index may be combined with any other index to create one index that provides information for two properties (e.g., sample-identification index, allele-locus index).

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; and Berg et al. (2002) *Biochemistry*, $5^{th}$ Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "an allele" refers to one or more copies of allele with various sequence variations, and reference to "the assay system" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The invention provides assay systems to identify copy number variants of nucleic acid regions (including loci, sets of loci and larger genomic regions, e.g., chromosomes), mutations, and polymorphisms in a genetic sample and/or to select a portion of a genetic sample for re-sequencing in a genetic sample.

In one aspect, the assay system utilizes methods to selectively identify and/or isolate selected nucleic acid regions from two or more genomic regions of interest (e.g., chromosomes or loci) in a genetic sample, and allows determination of an atypical copy number of a particular genomic region based on the comparison between the numbers of detected nucleic acid regions from the two or more chromosomes in the genetic sample or by comparison to one or more reference chromosomes from the same or a different sample.

More particularly, the assay system utilizes a tandem ligation method comprising the use of a first and second non-adjacent oligonucleotides of fixed sequence complementary to a selected nucleic acid region on a chromosome of interest or a reference chromosome, and one or more short, bridging oligonucleotides (also called "splint" oligos) complementary to the region between and immediately adjacent to the first and second oligonucleotides. Hybridization of these three or more oligonucleotides to a selected nucleic acid of interest, followed by ligation of these three or more oligonucleotides, provides a contiguous template for further amplification, detection and quantification of this region. The amplified regions may be quantified directly from the amplification reactions, or they are optionally isolated and identified to quantify the number of selected nucleic acid regions in a sample.

In specific aspects, the tandem ligation methods use fixed sequence oligonucleotides with a set of two or more contiguous, adjacent bridging oligonucleotides that hybridize to the region of the nucleic acid between the region complementary to the fixed sequence oligonucleotides. These bridging oligonucleotides hybridize adjacent to one another and to the fixed sequence oligonucleotides. The contiguous bridging oligonucleotides are ligated during the ligation reaction with the fixed sequence oligonucleotides and with each other, resulting in a single contiguous template for further amplification and sequence determination.

In other aspects of the invention, the assay system uses a set of oligonucleotides that bind to non-adjacent regions within a nucleic acid region of interest, and primer extension is utilized to created a contiguous set of hybridized oligos prior to the tandem ligation step. In such aspects, the assay system utilizes a tandem ligation method comprising the use of first and second non-adjacent oligonucleotides of fixed sequence complementary to a selected nucleic acid region on a chromosome of interest or a reference chromosome, and one or more short, bridging oligonucleotides complementary to the region between the first and second oligonucleotides but not immediately adjacent to one or the other fixed sequence oligonucleotide. Hybridization of these three or more oligonucleotides to a selected nucleic acid of interest is followed by an extension reaction using dNTPs and a polymerase to create a set of adjacent hybridized oligonucleotides, and ligation of the adjacent hybridized oligos. The combination of extension and ligation provides a contiguous template for further amplification, detection and quantification of this region. The amplified regions may be quantified directly from the amplification reactions, or they are optionally isolated and identified to quantify the number of selected nucleic acid regions in a sample.

In specific aspects, the tandem ligation methods use fixed sequence oligonucleotides with a set of two or more sequential but non-adjacent bridging oligonucleotides that hybridize to the region of the nucleic acid between the region complementary to the fixed sequence oligonucleotides. The "gap" regions between the fixed sequence oligonucleotides and the bridging oligos and/or between the sequential bridging oligonucleotides are ligated during the ligation reaction, resulting in a single contiguous template for further amplification and sequence determination.

In preferred aspects of the invention, the nucleic acids from the genetic sample are associated with a substrate, e.g., using binding pairs to attach the genetic material to a substrate surface. Briefly, a first member of a binding pair (e.g., biotin) can be associated with a nucleic acid of interest, and the associated nucleic acid attached to a substrate comprising a second member of a binding pair (e.g., avidin or streptavidin) on its surface. This can be particularly useful in removing any unhybridized oligonucleotides following specific binding of the fixed sequence oligonucleotides and/or the bridging oligonucleotides to the nucleic acid of interest. Briefly, the attached nucleic acids can be hybridized to the oligonucleotides, and the surface preferably treated to remove any unhybridized oligonucleotides, e.g., by washing or other removal methods such as degradation of such oligonucleotides as discussed in Willis et al., U.S. Pat. Nos. 7,700,323 and 6,858,412.

There are a number of methods that may be used in the association of a nucleic acid via binding pair interactions, as will be apparent to one skilled in the art upon reading the present specification. For example, numerous methods may be used for labeling the nucleic acids of a genetic sample with biotin, including random photobiotinylation, end-labeling with biotin, replicating with biotinylated nucleotides, and replicating with a biotin-labeled primer.

In a preferred aspect, the assay system of the invention employs a multiplexed reaction with a set of three or more such oligonucleotides for each selected nucleic acid region. This general aspect is illustrated in FIG. 1. Each set of oligonucleotides preferably contains two oligonucleotides 101, 103 of fixed sequence and one or more bridging oligonucleotides 113. Each of the fixed sequence oligonucleotides comprises a region complementary to the selected nucleic acid region 105, 107, and preferably universal primer sequences 109, 111, i.e. oligo regions complementary to universal primers. These universal primer sequences 109, 111 are used to amplify the different selected nucleic acid regions following ligation of the hybridized fixed sequence oligonucleotides and the bridging oligonucleotide. The universal primer sequences are located at or near the ends of the fixed sequence oligonucleotides 101, 103, and thus preserve the nucleic acid-specific sequences in the products of any universal amplification methods. Amplification products can be detected by determination of the sequence of the products, e.g., through sequence determination or hybridization, e.g., to an array or a bead-based detection system such as the Luminex™ bead-based assay (Invitrogen, Carlsbad, Calif.) or the BeadXpress™ assay (Illumina, San Diego, Calif.).

In one aspect of the assay systems of the invention, the fixed sequence oligonucleotides 101, 103 are introduced 102 to the genetic sample 100 and allowed to specifically bind to the complementary portions of the nucleic acid region of interest 115. Following hybridization, the unhybridized fixed sequence oligonucleotides are preferably separated from the remainder of the genetic sample (not shown). The bridging oligonucleotide is then introduced and allowed to bind 104 to the region of the selected nucleic acid region 115 between the first 101 and second 103 fixed sequence oligonucleotides. Alternatively, the bridging oligo can be introduced simultaneously to the fixed sequence oligonucleotides. The bound oligonucleotides are ligated 106 to create a contiguous nucleic acid spanning and complementary to the nucleic acid region of interest. Following ligation, universal primers 117, 119 are introduced to amplify 108 the ligated template region to create 110 products 121 that comprise the sequence of the nucleic acid region of interest. These products 121 are optionally isolated, detected, and quantified to provide information on the presence and amount of the selected nucleic acid region in a genetic sample. Preferably, the products are detected and quantified through sequence determination of the product, and in particular sequence determination of the region of the product corresponding to the selected nucleic acid region.

The number of selected nucleic acid regions analyzed for each chromosome in the assay system of the invention may vary from 2-20,000 or more per chromosome analyzed. In a preferred aspect, the number of targeted regions is between 48 and 480. In another aspect, the number of targeted regions is at least 100. In another aspect, the number of targeted regions is at least 400. In another aspect, the number of targeted regions is at least 1000.

In certain aspects, the bridging oligos can be composed of mixture of oligos with degeneracy in each of the positions, so that the mixture of randomers used will be compatible with all reactions in the multiplexed assay requiring a bridging of the given length. In another aspect, the bridging oligos can be of various lengths so that the mixture of oligos will be compatible with particular tandem ligation reactions in the multiplexed assay requiring bridging oligos of the given lengths.

In yet another aspect the bridging oligo can have partial degeneracy and the multiplexed tandem ligation reactions are restricted to those that require the specific sequences provided by the degeneracy of the bridging oligos. For example, a set of tandem ligation reactions may require only A and C bases in the bridging oligo, and a mixture of bridging oligos synthesized with only A and C bases would be provided for these particular tandem ligation reactions in a multiplexed assay.

In yet another aspect, the bridging oligo sequences are designed such that only those assays that have the given specific sequences in the bridging region would be multiplexed in the assay system. In one example the bridging oligo is a randomer, where all combinations of the bridging oligo are synthesized. As an example, in the case where a 5-base oligo is used, the number of unique bridging oligos would be $4^5=1024$. This would be independent of the number of targeted regions since all possible bridging oligos would be present in the reaction.

In another example the bridging oligo is specific, synthesized to match the sequences in the gap. As an example, in the case where a 5-base oligo is used, the number of unique oligos synthesized would be equal to or less than the number of targeted regions. A number less than the number of targeted regions could be achieved if the gap sequence was shared between two or more targeted regions. In one aspect of this example, one might purposefully choose the targeted sequences and especially the gap sequences such that there was as much identical overlap as possible in the gap sequences, minimizing the number of bridging oligos necessary for the multiplexed reaction.

In another aspect, the sequences of the bridging oligos are designed and the nucleic acid regions are selected so that all selected nucleic acid regions share the same base(s) at each end of the bridging oligo. For instance, one might choose selected nucleic acids and their gap location such that all of the gaps shared an "A" base at the first position and a "G" base at the last position of the gap. Any combination of a first and last base could be utilized, based upon factors such as the genome investigated, the likelihood of sequence variation in that area, and the like. In a specific aspect of this example, the bridging oligos can be synthesized by random degeneracy of bases at the internal positions of the bridging oligo, specific addition at the first and last position. In the case of a 5-mer, the second, third and fourth positions would be randomly provided, and two specific nucleotides would be added at the proximal positions. In this case, the number of unique bridging oligos would be 4^3=64.

In the human genome the frequency of the dinucleotide CG is much lower than expected by the respective mononucleotide frequencies. This presents an opportunity to enhance the specificity of an assay with a particular mixture of bridging oligos. In this aspect, the bridging oligos may be selected to have a 5' G and a 3' C. This base selection allows each oligo to have a high frequency in the human genome but makes it a rare event for two bridging oligos to hybridize adjacent to each other. The probability is then reduced that multiple oligos are ligated in locations of the genome that are not targeted in the assay.

The bridging oligo is preferably added to the reaction after the fixed sequence oligonucleotides have been hybridized, and following the optional removal of all unhybridized fixed sequence oligonucleotides have been washed away. The conditions of the hybridization reaction are preferably optimized near the $T_m$ of the bridging oligo to prevent erroneous hybridization of oligos that are not fully complementary to the nucleic acid region. If the bridging oligos have a $T_m$ significantly lower than the fixed sequence oligonucleotides, the splint oligo is preferably added as a part of the ligase reaction.

The advantage of using short oligos is that ligation on either end would likely occur only when all bases of the bridging oligo match the gap sequence. A further advantage of short bridging oligos is that the number of different oligos necessary could be less than the number of targeted sites, raising the oligos effective concentration to allow perfect matches to happen faster. Fewer oligos also has advantages in cost and quality control. The advantages of using fixed first and last bases with random bases in between include the ability to utilize longer bridging oligos for better specificity while reducing the number of total bridging oligos in the reaction.

Use of Indices in the Assay Systems of the Invention

In certain aspects, all or a portion of the nucleic acids of interest are directly detected using the described techniques. In certain aspects, however, the nucleic acids of interest are associated with one or more indices that are identifying for a selected nucleic acid region or a particular sample being analyzed. The detection of the one or more indices can serve as a surrogate detection mechanism of the selected nucleic acid region, or as confirmation of the presence of a particular selected nucleic acid region if both the index and the sequence of the nucleic acid region itself are determined. These indices are preferably associated with the selected nucleic acids during an amplification step using primers that comprise both the index and sequence regions that specifically hybridize to the nucleic acid region.

In one example, the primers used for amplification of a selected nucleic acid region are designed to provide a locus index between the selected nucleic acid region primer region and a universal amplification region. The locus index is unique for each selected nucleic acid region and representative of a locus on a chromosome of interest or reference chromosome, so that quantification of the locus index in a sample provides quantification data for the locus and the particular chromosome containing the locus.

In another aspect, the primers used for amplification of the selected nucleic acid regions to be analyzed for a genetic sample are designed to provide a random index between the selected nucleic acid region primer region and a universal amplification region. In such an aspect, a sufficient number of identification indices are present to uniquely identify each selected nucleic acid region in the sample. Each nucleic acid region to be analyzed is associated with a unique identification index, so that the identification index is uniquely associated with the selected nucleic acid region. Quantification of the identification index in a sample provides quantification data for the associated selected nucleic acid region and the chromosome corresponding to the selected nucleic acid region. The identification locus may also be used to detect any amplification bias that occurs downstream of the initial isolation of the selected nucleic acid regions from a sample.

In certain aspects, only the locus index and/or the identification index (if present) are detected and used to quantify the selected nucleic acid regions in a sample. In another aspect, a count of the number of times each locus index occurs with a unique identification index is done to determine the relative frequency of a selected nucleic acid region in a sample.

The primers are preferably designed so that indices comprising identifying information are coded at the ends of the primer flanking the region complementary to the nucleic acid of interest. The indices are non-complementary but unique sequences used within the primer to provide information relevant to the selective nucleic acid region that is isolated and/or amplified using the primer. The advantage of this is that information on the presence and quantity of the selected nucleic acid region can be obtained without the need to determine the actual sequence itself, although in certain aspects it may be desirable to do so. Generally, however, the ability to identify and quantify a selected nucleic acid region through identification of one or more indices will decrease the length of sequencing required as the loci information is captured at the 3' or 5' end of the isolated selected nucleic acid region. Use of indices as a surrogate for identification of selected nucleic acid regions may also reduce error since longer sequencing reads are more prone to the introduction or error.

In addition to locus-specific indices and identification indices, additional indices can be introduced to primers to assist in the multiplexing of samples. In addition, indices which identify sequencing error, which allow for highly multiplexed amplification techniques or which allow for hybridization or ligation or attachment to another surface can be added to the primers. The order and placement of these indices, as well as the length of these indices, can vary.

The primers used for identification and quantification of a selected nucleic acid region may be associated with regions complementary to the 5' of the selected nucleic acid region, regions complementary to the 5' of the selected nucleic acid region, or in certain amplification regimes the indices may be present on one or both of a set of amplification primers complementary to the selected nucleic acid region. The primers can be used to multiplex the analysis of multiple selected nucleic acid regions to be analyzed within a sample, and can be used either in solution or on a solid substrate, e.g., on a microarray or on a bead. These primers may be used for linear replication or amplification, or they may create circular constructs for further analysis.

Thus, in some aspects one or both of the fixed sequence oligonucleotides further contain an index region. This index region may comprise a number of different sequences that can be used to identify the selected nucleic acid region and/or the sample being analyzed in the assay system. Preferably, the index region corresponds to the selected nucleic acid region, so that identification of the index region can be used as a surrogate for detection of the actual sequence of the selected nucleic acid region. The index region may optionally comprise a sample index to correspond the oligo set to a particular genetic sample in a multiplexed assay system.

Figure 2:
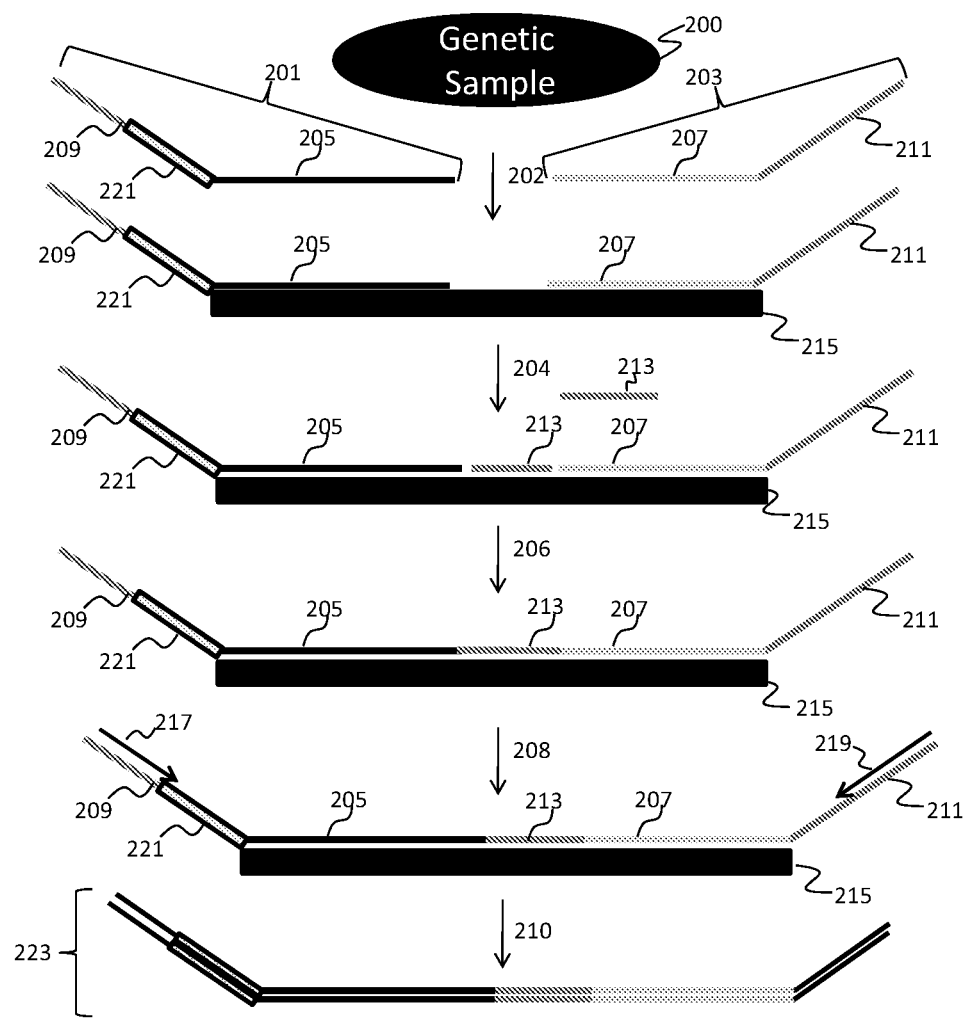
FIG. 2 illustrates a second general schematic for a ligation-based assay system of the invention.

FIG. 2 illustrated the use of a single index region 221 on a first fixed sequence oligonucleotide 201 in an oligo set for a selected nucleic acid region. The fixed sequence oligonucleotides 201, 203 are introduced 202 to the genetic sample 200 and allowed to specifically bind to the selected nucleic acid region 215. Following hybridization, the unhybridized fixed sequence oligonucleotides are preferably separated from the remainder of the genetic sample (not shown). The bridging oligo is then introduced and allowed to hybridize 204 to the region of the selected nucleic acid region 215 between the first 201 and second 203 fixed sequence oligonucleotides. The bound oligonucleotides are ligated 206 to create a contiguous nucleic acid spanning and complementary to the nucleic acid region of interest. Following ligation, universal primers 217, 219 are introduced to amplify 208 the ligated template region to create 210 products 223 that comprise the sequence of the nucleic acid region of interest. These products 223 are optionally isolated, detected, and/or quantified to provide information on the presence and amount of the selected nucleic acid region in a genetic sample. Preferably, the products are detected and quantified through sequence determination of the index, thus obviating the need for determining the actual sequences of the selected nucleic acid region. In other aspects, however, it is desirable to determine the product comprising sequences of both the index and the selected nucleic acid region, for example, to provide internal confirmation of the results or where the index provides sample information and is not informative of the selected nucleic acid region. In another aspect, the index permits unique hybridization to a feature on an array, such hybridization leading to the detection and quantification of the sequences.

Figure 3:
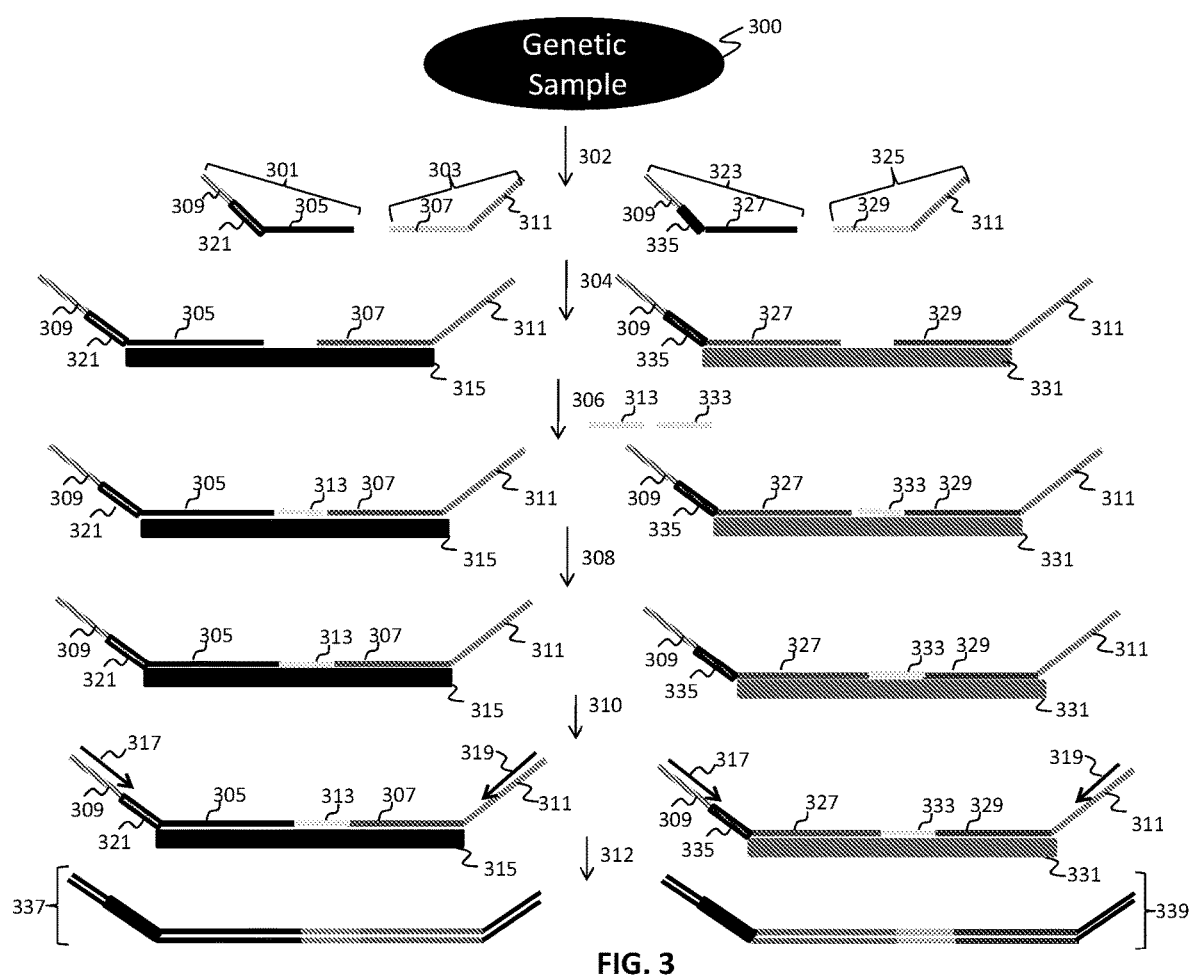
FIG. 3 illustrates a multiplexed assay system for detection of two or more regions of interest.

The use of indices is especially useful in a multiplexed assay setting where two or more different selected nucleic acid regions are being simultaneously detected in a genetic sample. FIG. 3 illustrates an example where two different selected nucleic acid regions are detected in a single tandem reaction assay. Two sets of fixed sequence oligonucleotides (301 and 303, 323 and 325) that specifically hybridize to two different nucleic acid regions 315, 331 are introduced 302 to a genetic sample and allowed to hybridize 304 to the respective nucleic acid regions. Each set comprises an oligonucleotide 301, 323 having a sequence specific region 305, 327, a universal primer region 309 and an index region 321, 335. The other fixed sequence oligonucleotide of the sets comprise a sequence specific region 307, 329 and a universal primer region 311. Following hybridization, the unhybridized fixed sequence oligonucleotides are preferably separated from the remainder of the genetic sample (not shown). The bridging oligos 313, 333 are introduced to the hybridized fixed sequence oligonucleotide/nucleic acid regions and allowed to hybridize 306 to these regions. Although shown in FIG. 3 as two different bridging oligos, in fact the same bridging oligo may be suitable for both hybridization events, or they may be two oligos from a pool of degenerate oligos that are used with multiple tandem ligation events. The bound oligonucleotides are ligated 308 to create a contiguous nucleic acid spanning and complementary to the nucleic acid region of interest. Following ligation, universal primers 317, 319 are introduced to amplify 310 the ligated template regions to create 312 amplification products 337, 339 that comprise the sequence of the nucleic acid regions of interest. These products 337, 339 are optionally isolated, detected and/or quantified to provide information on the presence and amount of the selected nucleic acid region in a genetic sample.

In multiplexed assay systems, the products are detected and quantified through sequence determination of the different indices, thus obviating the need for determining the actual sequences of the selected nucleic acid region. In other aspects, however, the index may be a sample specific index as well as a region specific index, and thus the index may not only identify the nucleic acid region, but it may also provide information of the nucleic acid region and the genetic sample from which the region was obtained. Alternatively, the nucleic acid region of the product may be detected, for example, to provide internal confirmation of the results or where the index provides solely sample information and is not informative of the selected nucleic acid region.

Detection of Polymorphic Regions Using the Ligation-Based Assay System

In certain aspects, the assay system of the invention detects one or more regions that comprises a polymorphism. This methodology is not primarily designed to identify a particular allele, e.g., as maternal versus fetal, but rather to ensure that different alleles corresponding to a nucleic acid region of interest are included in the quantification methods of the invention. In certain aspects, however, it may be desirable to both use the information to count all such nucleic acid regions in the genetic sample as well as to use the information on specific polymorphisms, e.g., to calculate the amount of fetal DNA contained within a maternal sample, or identify the % alleles with a particular mutation in a genetic sample from a cancer patient. Thus, the invention is intended to encompass both mechanisms for detection of SNP-containing nucleic acid regions for direct determination of copy number variant through quantification as well as detection of SNP for ensuring overall efficiency of the assay.

Thus, in a particular aspect of the invention, allele-discrimination is provided through the bridging oligo. In this aspect, the bridging oligo is located over a SNP. In this aspect, the polymorphism is preferably located close enough to one end of a ligation reaction as to provide allele-specificity.

Figure 4:
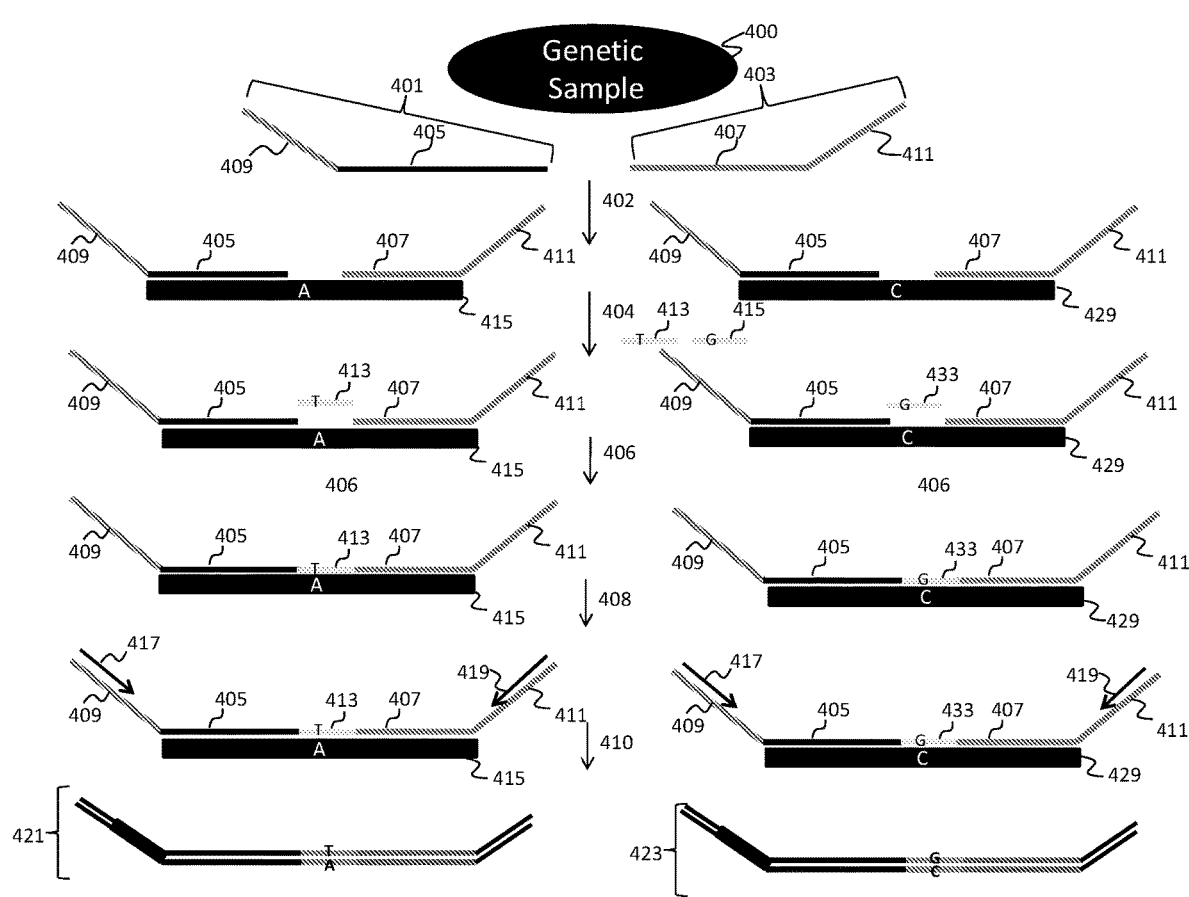
FIG. 4 illustrates a first multiplexed assay system for detection of two or more alleles within a region of interest.

In one example of allele detection, both complementary allele bridging oligo variants are present in the same reaction mixture and allele detection results from subsequent sequencing through the polymorphism of the ligated products or their amplification products. FIG. 4 illustrates this aspect.

In FIG. 4, two fixed sequence oligonucleotides 401, 403 and bridging oligonucleotides corresponding to the two possible SNPs in the nucleic acid regions of interest 415, 429 are used in detection of the selected nucleic acid region, and preferably to detect the region in a single reaction. Each of the fixed sequence oligonucleotides comprises a region complementary to the selected nucleic acid region 405, 407, and universal primer sequences 409, 411 used to amplify the different selected nucleic acid regions following initial selection and/or isolation of the selected nucleic acid regions from the genetic sample. The universal primer sequences are located at the proximal ends of the fixed sequence oligonucleotides 401, 403, and thus preserve the nucleic acid-specific sequences in the products of any universal amplification methods. The fixed sequence oligonucleotides 401, 403 are introduced 402 to the genetic sample 400 and allowed to specifically bind to the selected nucleic acid region 415, 429. Following hybridization, the unhybridized fixed sequence oligonucleotides are preferably separated from the remainder of the genetic sample (not shown). The bridging oligos corresponding to an A/T SNP 413 or a G/C SNP 433 are introduced and allowed to bind 404 to the region of the selected nucleic acid region 415, 429 between the first 401 and second 403 fixed sequence oligonucleotides. Alternatively, the bridging oligos 413, 433 can be introduced to the sample simultaneously with the fixed sequence oligonucleotides.

The bound oligonucleotides are ligated 406 to create a contiguous nucleic acid spanning and complementary to the nucleic acid region of interest. Following ligation, universal primers 417, 419 are introduced to amplify 408 the ligated template region to create 410 products 421, 423 that comprise the sequence of the nucleic acid region of interest representing both SNPs in the selected nucleic acid region. These products 421, 423 are detected and quantified through sequence determination of the product, and in particular the region of the product containing the SNP in the selected nucleic acid region.

In another example, the allele detection results from the sequencing of a locus index or an allele index which is provided in one or both of the fixed sequence nucleic acid region oligonucleotides. The locus index and/or allele index is embedded in either the first or second fixed sequence oligonucleotide used in the set for a selected nucleic acid region containing a polymorphism, and is used with either a specific fixed sequence oligo or with a particular bridging oligo, either of which may be designed to detect the polymorphism. Detection of the locus index and/or the allele index in an amplification product allows detection of the presence, amount or absence of a specific allele present in a genetic sample, as well as the number of counts for the region through addition of the polymorphic regions detected in the sample. Two examples of how this may be performed are described in more detail below.

For example, in one aspect of the invention, two or more separate reactions are carried out using a single locus index and different bridging oligos corresponding to the different polymorphisms in the region complementary to the bridging oligos. The reactions are differentiated by the bridging oligo, and the ligation, amplification and detection reactions comprising the different bridging oligos remain separate through the detection step. The total counts for a particular nucleic acid region of interest can be determined mathematically using the locus index by adding the detected numbers of the counts for the nucleic acid region from the separate reactions comprising the bridging oligos having different polymorphic sequences.

This aspect may be useful for, e.g., circumstances in which both information on polymorphic frequency in a sample and information on total loci counts are desirable. Since the reactions are detected separately, only one index may be needed for detection in each of the separate reactions, although separate allele indices may also be used in the separate reactions.

Figure 5:
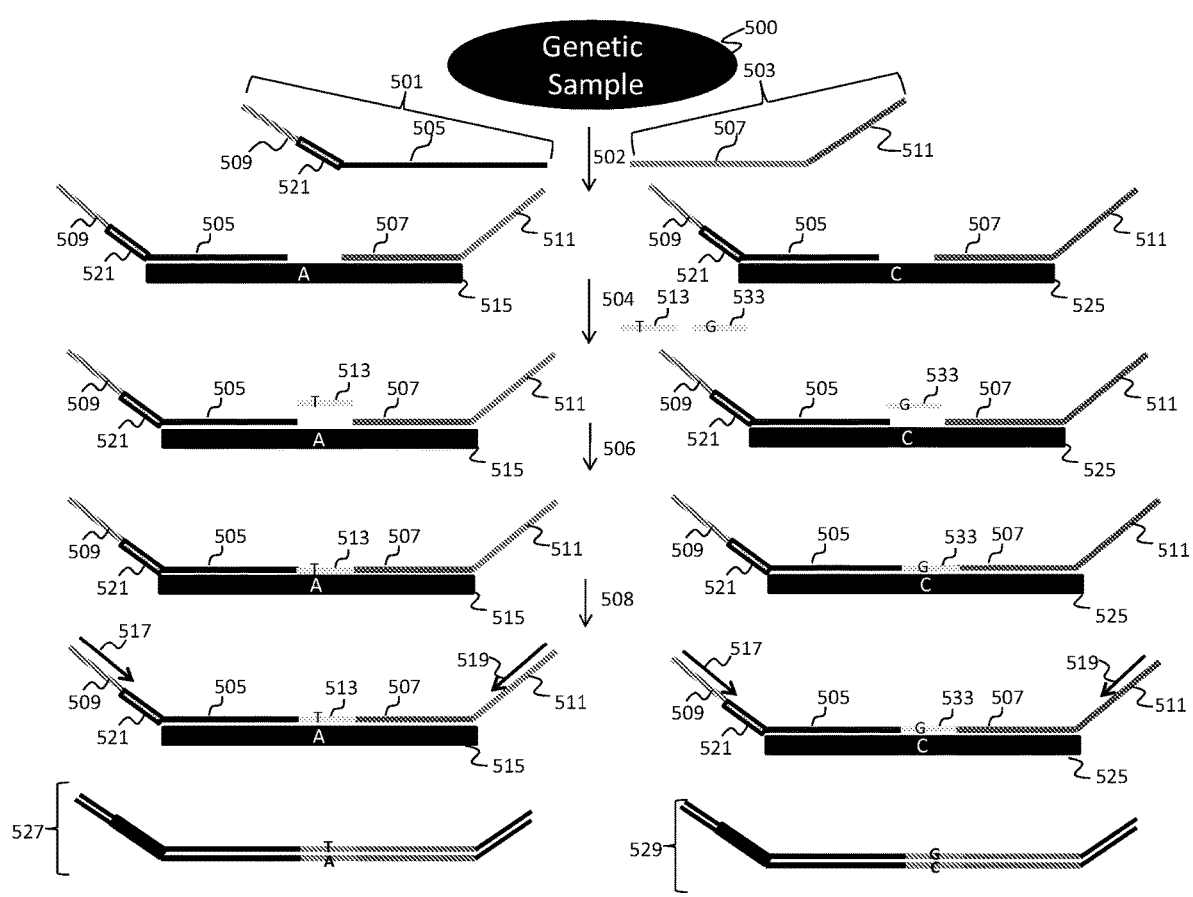
FIG. 5 illustrates a second multiplexed assay system for detection of two or more alleles within a region of interest.

FIG. 5 illustrates one such aspect of the assay system of the invention. Two fixed sequence oligonucleotides 501, 503 and bridging oligonucleotides corresponding to the two possible SNPs in the selected nucleic acid region 515, 525 are used in detection of a nucleic acid region of interest. Each of the fixed sequence oligonucleotides comprises a region complementary to the selected nucleic acid region. The ligation, amplification, and detection steps of the assay system take place in two separate reactions, with a first reaction utilizing a first bridging oligo 513 and the second reaction utilizing a second bridging oligo 533. Both reactions utilize the same fixed sequence oligos 501, 503 having the same regions complementary to allele-specific regions 505, 507. A single locus index 521 can be used to detect the amplification products in each reaction so that sequence determination of the actual sequence of the nucleic acids of interest are not necessarily needed, although they may still be determined to identify or provide confirmation of the sequence. The universal primer sequences 509, 511 are located at either end flanking the fixed sequence oligonucleotides 501, 503, and thus preserve the nucleic acid-specific sequences and the indices in the products of any universal amplification methods. The fixed sequence oligonucleotides 501, 503 are introduced 502 to the genetic sample 500 and allowed to specifically bind to the selected nucleic acid region 515, 525. Following hybridization, the unhybridized fixed sequence oligonucleotides are preferably separated from the remainder of the genetic sample (not shown). The bridging oligos corresponding to an A/T SNP 513 or a G/C SNP 533 are introduced to each reaction and allowed to bind 504 to the region of the selected nucleic acid region 515, 525 between the first 505 and second 507 fixed sequence oligonucleotides. Alternatively, the bridging oligos 513, 533 can be introduced to the sample simultaneously with the fixed sequence oligonucleotides.

The bound oligonucleotides are ligated 506 to create a contiguous nucleic acid spanning and complementary to the nucleic acid region of interest. Following ligation, universal primers 517, 519 are introduced to amplify 508 the ligated template region to create 510 products 527, 529 that comprise the sequence of the nucleic acid region of interest representing both SNPs in the selected nucleic acid region. These products 527, 529 are detected and quantified through sequence determination of the product, and in particular the locus index combined with the knowledge of which bridging oligo was added to which reaction. The counts for the nucleic acid region as a whole can be determined through addition of the detected polymorphic regions in the genetic samples.

A different specific aspect of the invention utilizes allele indices to indentify alleles comprising different polymorphisms as well as to determine counts of the nucleic acid region of interest. In a multiplexed reaction, locus indices may be combined with allele indices. In this aspect, two or more separate ligation reactions are carried out using two or more different bridging oligos corresponding to the different polymorphisms in the region complementary to the bridging oligos. The reactions are differentiated by the bridging oligo, and each bridging oligo is used with a fixed sequence oligo comprising an allele index that identifies that particular bridging oligo. Following the ligation step, the reactions can be combined either prior to amplification, since the same universal primers are preferably used, or prior to detection, as the different alleles can be distinguished through identification of the different allele-specific indices. The allele may also be distinguished through sequence determination of the allele index or alternatively from hybridizing of the allele index, and total counts for the nucleic acid region can be determined through the addition of the identified allelic regions.

Figure 6:
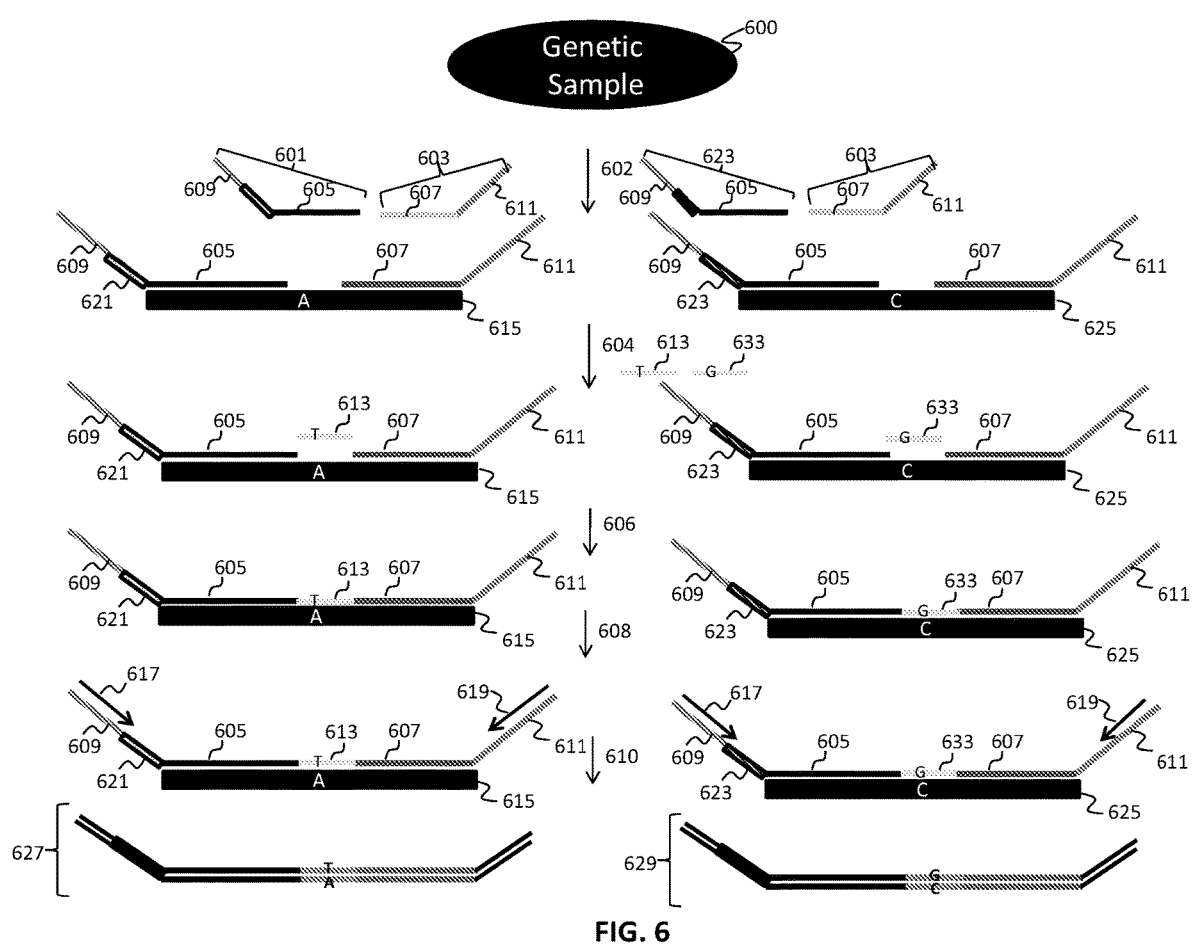
FIG. 6 illustrates a third multiplexed assay system for detection of two or more alleles within a region of interest.

In FIG. 6, two fixed sets of sequence oligonucleotides are used which comprise substantially the same sequence-specific regions 605, 607 but which comprise different indices, 621, 623 on one of the fixed sequence oligonucleotides of the set. The ligation reactions are carried out with material from the same genetic sample 600, but in separate tubes with the different allele-specific oligo sets. The bridging oligonucleotides corresponding to the two possible SNPs in the selected nucleic acid region 613, 633 are used in detection of the selected nucleic acid region in each ligation reaction. Two allele indices 621, 623 that are indicative of the particular polymorphic alleles can be used to detect the amplification products so that sequence determination of the actual sequence of the nucleic acids of interest are not necessarily needed, although these sequences may still be determined to identify and/or provide confirmation of the sequence. Each of the fixed sequence oligonucleotides comprises a region complementary to the selected nucleic acid region 605, 607, and universal primer sequences 609, 611 used to amplify the different selected nucleic acid regions following initial selection and/or isolation of the selected nucleic acid regions from the genetic sample. The universal primer sequences are located at the ends of the fixed sequence oligonucleotides 601, 603, and 623 flanking the indices and the regions complementary to the nucleic acid of interest, thus preserving the nucleic acid-specific sequences and the allele indices in the products of any universal amplification methods. The fixed sequence oligonucleotides 601, 603, 623 are introduced 602 to an aliquot of the genetic sample 600 and allowed to specifically bind to the selected nucleic acid regions 615 or 625. Following hybridization, the unhybridized fixed sequence oligonucleotides are preferably separated from the remainder of the genetic sample (not shown).

The bridging oligos corresponding to an A/T SNP 613 or a G/C SNP 633 are introduced and allowed to bind 604 to the region of the selected nucleic acid region 615 or 625 between the first 605 and second 607 nucleic acid-complementary regions of the fixed sequence oligonucleotides. Alternatively, the bridging oligos 613, 633 can be introduced to the sample simultaneously with the fixed sequence oligonucleotides. The bound oligonucleotides are ligated 606 in the single reaction mixture to create a contiguous nucleic acid spanning and complementary to the nucleic acid region of interest.

Following ligation, the separate reactions are preferably combined for the universal amplification and detection steps. Universal primers 617, 619 are introduced to the combined reactions to amplify 608 the ligated template regions and create 610 products 627, 629 that comprise the sequence of the nucleic acid region of interest representing both SNPs in the selected nucleic acid region. These products 627, 629 are detected and quantified through sequence determination of the product, through the allele index and/or the region of the product containing the SNP in the selected nucleic acid region.

Preferably, the products of the FIG. 6 methods are detected and quantified through sequence determination of the allele indices, thus obviating the need for determining the actual sequences of the selected nucleic acid region. In other aspects, however, it is desirable to determine the product comprising sequences of both the index and the selected nucleic acid region, for example, to provide internal confirmation of the results or where the index provides sample information and is not informative of the selected nucleic acid region.

The indices used with the assay systems of the invention can also be used to identify polymorphisms that are associated with the fixed sequences used for the detection of nucleic acids of interest. Thus, in another exemplary assay system, an allele index is associated with an allele-specific fixed sequence oligonucleotide, and the allele detection results from the sequencing of an allele index or alternatively from hybridizing of an allele index which is provided in the nucleic acid region primer. The allele index is embedded in either the allele-specific first or second fixed sequence oligonucleotide used in the set for a selected nucleic acid region containing a polymorphism. In specific aspects, an allele index is present on both the first and second fixed sequence oligonucleotides to detect two or more polymorphisms within the fixed sequence regions. The number of fixed sequence oligonucleotides used in such aspects can corresponds to the number of possible alleles being assessed for a selected nucleic acid region, and sequence determination or hybridization of the allele index can detect presence, amount or absence of a specific allele is a genetic sample.

Figure 7:
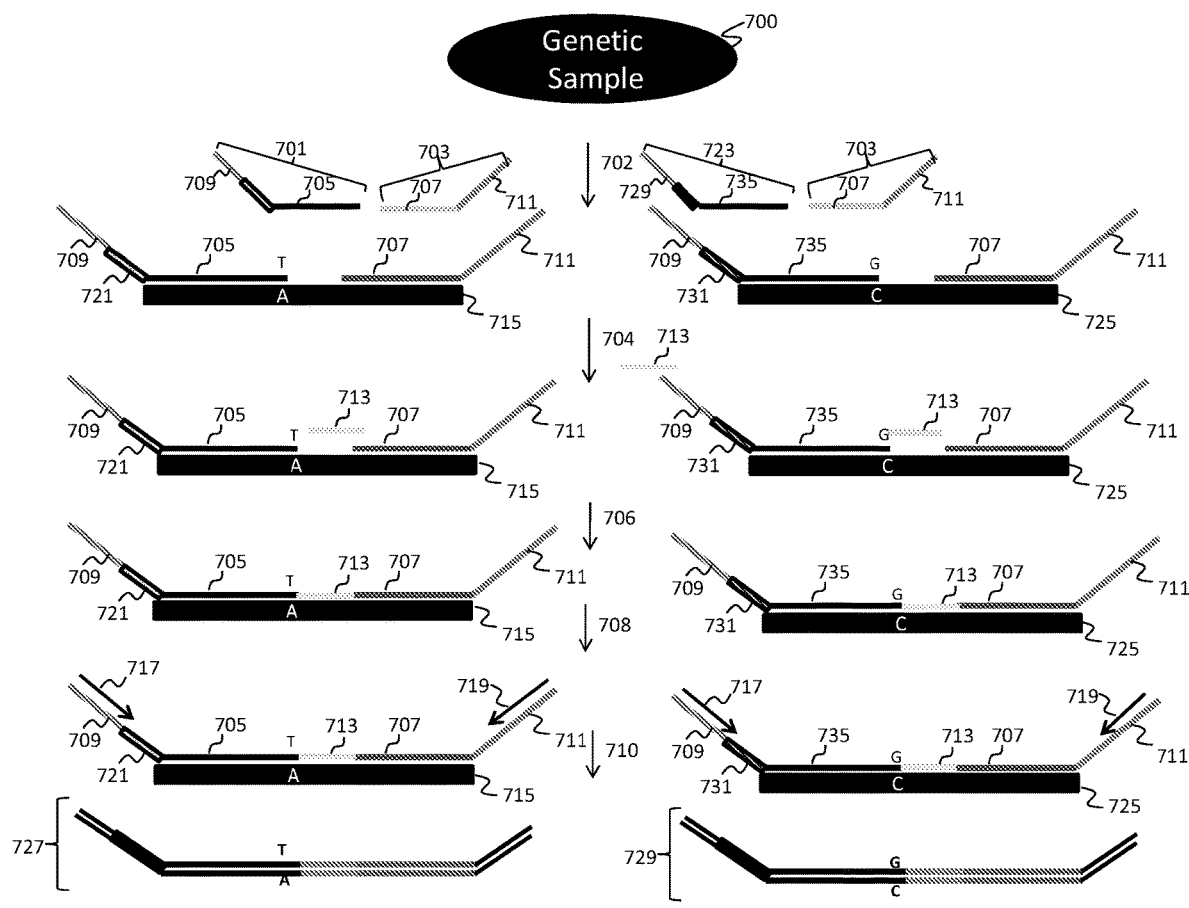
FIG. 7 illustrates a fourth multiplexed assay system for detection of two or more alleles within a region of interest.

FIG. 7 illustrates this aspect of the invention. In FIG. 7, three fixed sequence oligonucleotides 701, 703 and 723 are used. Two of the fixed sequence oligonucleotides 701, 723 are allele-specific, comprising a region complementary to an allele in a nucleic acid region comprising for example an A/T or G/C SNP, respectively. Each fixed allele-specific oligonucleotides 701, 723 also comprises a corresponding allele index 721, 731 and a universal primer sequence 709. The second fixed sequence oligonucleotide 703 has another universal primer sequence 711, and these universal primer sequences are used to amplify the \nucleic acid regions following initial selection and/or isolation of the nucleic acid regions from the genetic sample. The universal primer sequences are located at the ends of the fixed sequence oligonucleotides 701, 703, 723 flanking the indices and the nucleic acid regions of interest, and thus preserve the nucleic acid-specific sequences and the indices in the products of any universal amplification methods.

The fixed sequence oligonucleotides 701, 703, 723 are introduced 702 to the DNA sample 700 and allowed to specifically bind to the selected nucleic acid region 715, 725. Following hybridization, the unhybridized fixed sequence oligonucleotides are preferably separated from the remainder of the genetic sample (not shown). The bridging oligos 713 are introduced and allowed to bind 704 to the nucleic acid 715 complementary to the region between the first allele-specific fixed sequence oligonucleotide region 705 and the other fixed sequence oligonucleotide region 707 or to the nucleic acid 725 complementary to the region between the second allele-specific fixed sequence oligonucleotide region 735 and the other fixed sequence oligonucleotide region 707. Alternatively, the bridging oligos 713 can be introduced to the sample simultaneously with the sets of fixed sequence oligonucleotides.

The bound oligonucleotides are ligated 706 to create a contiguous nucleic acid spanning and complementary to the nucleic acid region of interest. The ligation primarily occurs only when the allele-specific ends match. Following ligation, universal primers 717, 719 are introduced to amplify 708 the ligated template region to create 710 products 727, 729 that comprise the sequence of the nucleic acid region of interest representing both SNPs in the selected nucleic acid region. These products 727, 729 are detected and quantified through sequence determination of the product, and in particular the region of the product containing the SNP in the selected nucleic acid region. Alternatively the products 727, 729 are detected and quantified through hybridization of the allele index to different features on an array. In this detection method, a fluorescent label is incorporated into the products 727, 729 during the universal amplification by amplifying with primers 717 or 719 that are fluorescently labeled. It is important to note that the ligation 706 is allele-specific. In order to make the ligation allele-specific, the allele specifying nucleotide must be close to the ligated end. Typically, the allele-specific nucleotide must be within 5 nucleotides of the ligated end. In a preferred aspect, the allele-specific nucleotide is the terminal base.

Figure 8:
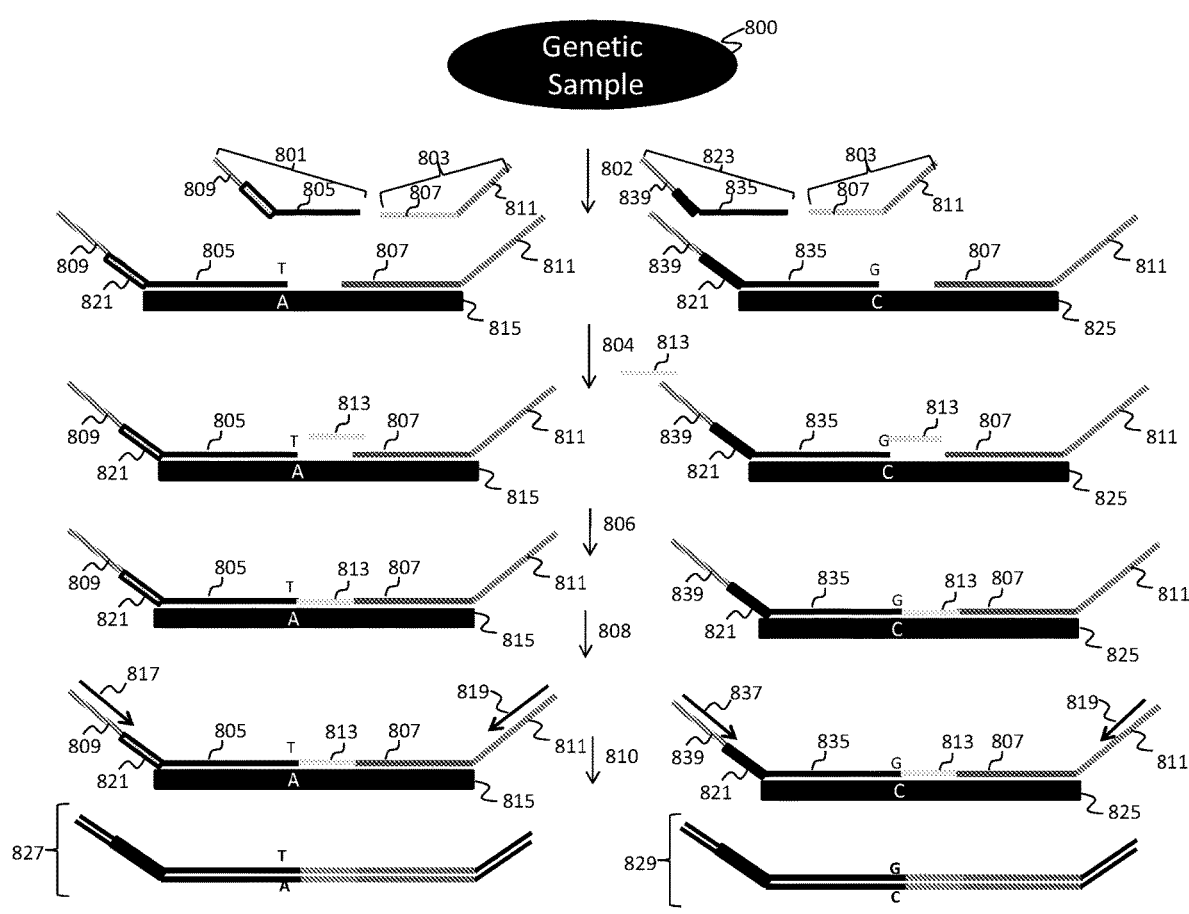
FIG. 8 illustrates a fifth multiplexed assay system for detection of two or more alleles within a region of interest.

In another example, the allele detection results from the hybridization of a locus index to an array. Each allele is detected through an allele-specific labeling step, where each allele is labeled with a spectrally distinct fluorescent label during the universal amplification. FIG. 8 illustrates this aspect of the invention. In FIG. 8, three fixed sequence oligonucleotides 801, 803 and 823 are used. Two of the fixed sequence oligonucleotides 801, 823 are allele-specific comprising a region matching a particular allele in the same selected nucleic acid region, a corresponding locus index 821 and allele-specific universal primer sequences 809, 839. The matching fixed sequence oligonucleotide 803 has another universal primer sequence 811. The universal primer sequences are used to amplify the different selected nucleic acid regions following initial selection and/or isolation of the selected nucleic acid regions from the genetic sample and incorporate a label into the amplification products that distinguish each allele. The universal primer sequences are located at the proximal ends of the fixed sequence oligonucleotides 801, 803, 823 and thus preserve the nucleic acid-specific sequences and the indices in the products of any universal amplification methods. The fixed sequence oligonucleotides 801, 803, 823 are introduced 802 to the DNA sample 800 and allowed to specifically bind to the selected nucleic acid region 815, 825. Following hybridization, the unhybridized fixed sequence oligonucleotides are preferably separated from the remainder of the genetic sample (not shown). The bridging oligos 813 are introduced and allowed to bind 804 to the region of the selected nucleic acid region 815, 825 between the first 805 and second 807 fixed sequence oligonucleotides and between the first 835 and second 807 fixed sequence oligonucleotides. Alternatively, the bridging oligos 813 can be introduced to the sample simultaneously with the fixed sequence oligonucleotides.

The bound oligonucleotides are ligated 806 to create a contiguous nucleic acid spanning and complementary to the nucleic acid region of interest. The ligation primarily occurs only when the allele-specific ends match. Following ligation, universal primers 817, 819, 837 are introduced to amplify 808 the ligated template region to create 810 products 827, 829 that comprise the sequence of the nucleic acid region of interest representing both SNPs in the selected nucleic acid region. The universal primers 817 and 837 have spectrally distinct fluorescent labels such that the allele-specific information is retained through these fluorescent labels. These products 827, 829 are detected and quantified through hybridization of the locus index 821 to an array and imaging to determine the incorporation of the fluorescent label. It is important to note that the ligation 806 is preferably allele-specific. In order to make the ligation allele-specific, the allele specifying nucleotide must be close to the ligated end. Typically, the allele-specific nucleotide must be within 5 nucleotides of the ligated end. In a preferred aspect, the allele-specific nucleotide is the terminal base.

In another aspect, an allele index is present on both the first and second fixed sequence oligonucleotides to detect a polymorphism at both ends with a corresponding spectrally distinct fluorescent label for each fixed sequence oligonucleotide for a given allele. The number of fixed sequence oligonucleotides corresponds to the number of possible alleles being assessed for a selected nucleic acid region. In the above figures and examples, the fixed sequence oligonucleotides are represented as two distinct oligonucleotides. In another aspect, the fixed sequence oligonucleotides may be opposite ends of the same oligonucleotide.

In the aspects described above, the bridging oligos used hybridize to regions of the nucleic acid of interest that are adjacent to the regions complementary to the fixed sequence oligonucleotides, so that when the fixed sequence and bridging oligo(s) specifically hybridize they are directly adjacent to one another for ligation. In other aspects, however, the bridging oligo hybridizes to a region that is not directly adjacent to the region complementary to one or both of the fixed sequence oligos, and an intermediate step requiring extension of one or more of the oligos is necessary prior to ligation.

Figure 9:
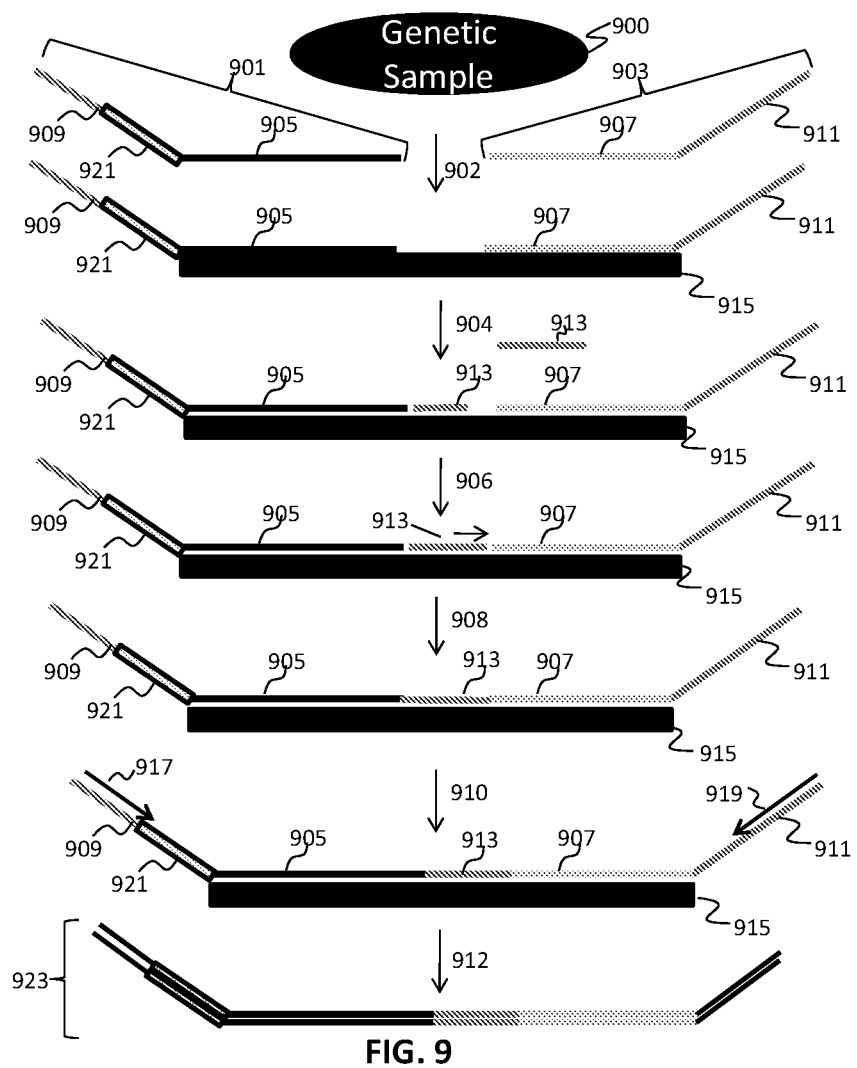
FIG. 9 illustrates a first general schematic for assay system utilizing oligo extension in a ligation-based assay system of the invention.

For example, as illustrated in FIG. 9, each set of oligonucleotides preferably contains two oligonucleotides 901, 903 of fixed sequence and one or more bridging oligonucleotides 913. Each of the fixed sequence oligonucleotides comprises a region complementary to the selected nucleic acid region 905, 907, and preferably universal primer sequences 909, 911, i.e. oligo regions complementary to universal primers. The universal primer sequences 909, 911 are located at or near the ends of the fixed sequence oligonucleotides 901, 903, and thus preserve the nucleic acid-specific sequences in the products of any universal amplification methods. The fixed sequence oligonucleotides 901, 903 are introduced 902 to the genetic sample 900 and allowed to specifically bind to the complementary portions of the nucleic acid region of interest 915. Following hybridization, the unhybridized fixed sequence oligonucleotides are preferably separated from the remainder of the genetic sample (not shown). The bridging oligonucleotide is then introduced and allowed to bind 904 to the region of the selected nucleic acid region 915 between the first 901 and second 903 fixed sequence oligonucleotides. Alternatively, the bridging oligo can be introduced simultaneously to the fixed sequence oligonucleotides. In this exemplary aspect, the bridging oligo hybridizes to a region directly adjacent to the first fixed sequence oligo region 905, but is separated by one or more nucleotides from the complementary region of the second fixed sequence oligonucleotide 907. Following hybridization of the fixed sequence and bridging oligos, the bridging oligo 913 is extended 906, e.g., using a polymerase and dNTPs, to fill the gap between the bridging oligo 913 and the second fixed sequence oligo 903. Following extension, the bound oligonucleotides are ligated 908 to create a contiguous nucleic acid spanning and complementary to the nucleic acid region of interest 915. After ligation, universal primers 917, 919 are introduced 910 to amplify the ligated template region to create 912 products 923 that comprise the sequence of the nucleic acid region of interest. These products 923 are optionally isolated, detected, and quantified to provide information on the presence and amount of the selected nucleic acid region in a genetic sample. Preferably, the products are detected and quantified through sequence determination of an identification index 921, or, alternatively, sequence determination of the nucleic acid of interest 915 within the amplification product 923.

Figure 10:
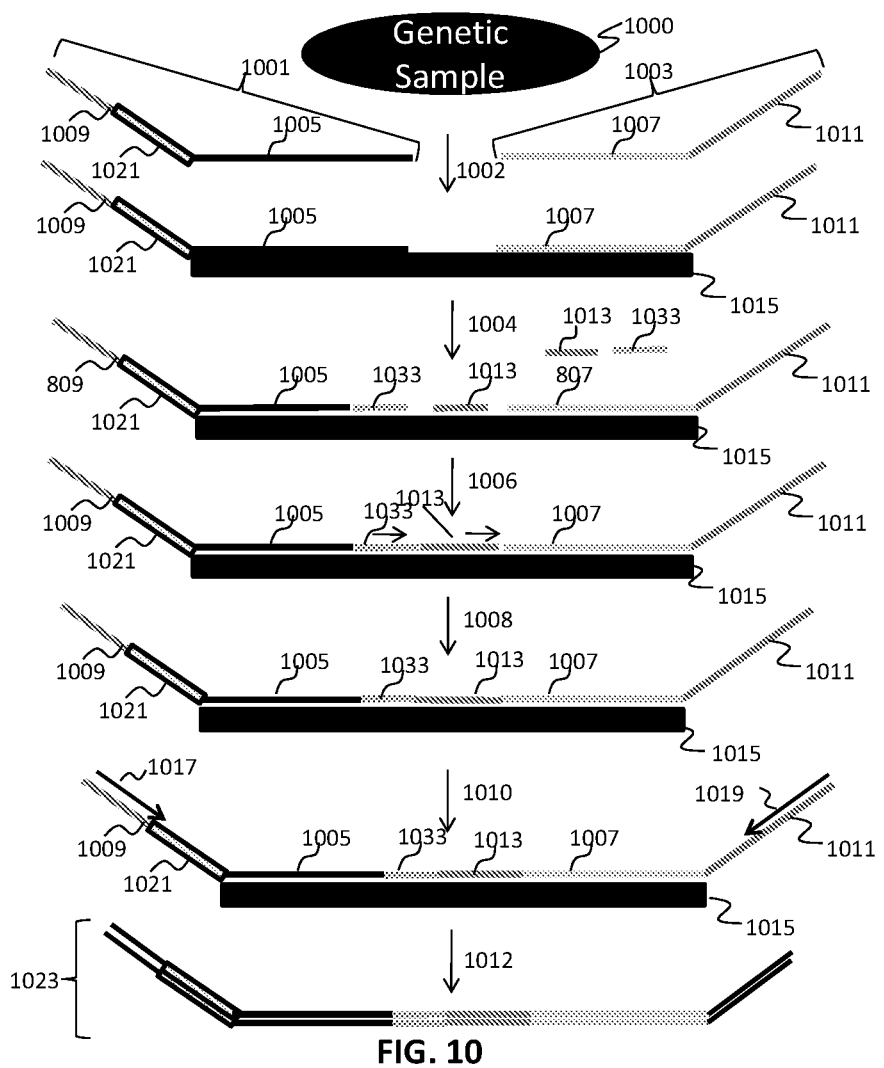
FIG. 10 illustrates a second general schematic for assay system utilizing oligo extension in a ligation-based assay system of the invention.

In another aspect, as illustrated in FIG. 10, each set of oligonucleotides preferably contains two oligonucleotides 1001, 1003 of fixed sequence and two or more bridging oligonucleotides 1013, 1033 that bind to non-adjacent regions on a nucleic acid of interest 1015. Each of the fixed sequence oligonucleotides comprises a region complementary to the selected nucleic acid region 1005, 1007, and preferably universal primer sequences 1009, 1011, i.e. oligo regions complementary to universal primers. The universal primer sequences 1009, 1011 are located at or near the ends of the fixed sequence oligonucleotides 1001, 1003, and thus preserve the nucleic acid-specific sequences in the products of any universal amplification methods. The fixed sequence oligonucleotides 1001, 1003 are introduced 1002 to the genetic sample 1000 and allowed to specifically bind to the complementary portions of the nucleic acid region of interest 1015. Following hybridization, the unhybridized fixed sequence oligonucleotides are preferably separated from the remainder of the genetic sample (not shown).

In FIG. 10, two separate bridging oligonucleotides 1013, 1033 are introduced and allowed to bind 1004 to the region of the selected nucleic acid region 1015 between but not immediately adjacent to both the first 1001 and second 1003 fixed sequence oligonucleotides. Alternatively, the bridging oligo can be introduced simultaneously to the fixed sequence oligonucleotides. In this exemplary aspect, the first bridging oligo 1033 hybridizes to a region directly adjacent to the first fixed sequence oligo region 1005, but is separated by one or more nucleotides from the complementary region of the second bridging oligo 1013. The second bridging oligo 1013 is also separated from the second fixed sequence oligonucleotide 1007 by one or more nucleotides. Following hybridization of the fixed sequence and bridging oligos, both bridging oligos 1013, 1033 are extended 1006, e.g., using a polymerase and dNTPs, to fill the gap between the bridging oligos and the gap between the second bridging oligo 1013 and the second fixed sequence oligo 1003. Following extension, the bound oligonucleotides are ligated 1008 to create a contiguous nucleic acid spanning and complementary to the nucleic acid region of interest 1015. Following ligation, universal primers 1017, 1019 are introduced 910 to amplify the ligated template region to create 1012 products 1023 that comprise the sequence of the nucleic acid region of interest. These products 1023 are optionally isolated, detected, and quantified to provide information on the presence and amount of the selected nucleic acid region in a genetic sample. Preferably, the products are detected and quantified through sequence determination of an identification index 1021, or, alternatively, sequence determination of the nucleic acid of interest 1015 within the amplification product 1023.

Figure 11:
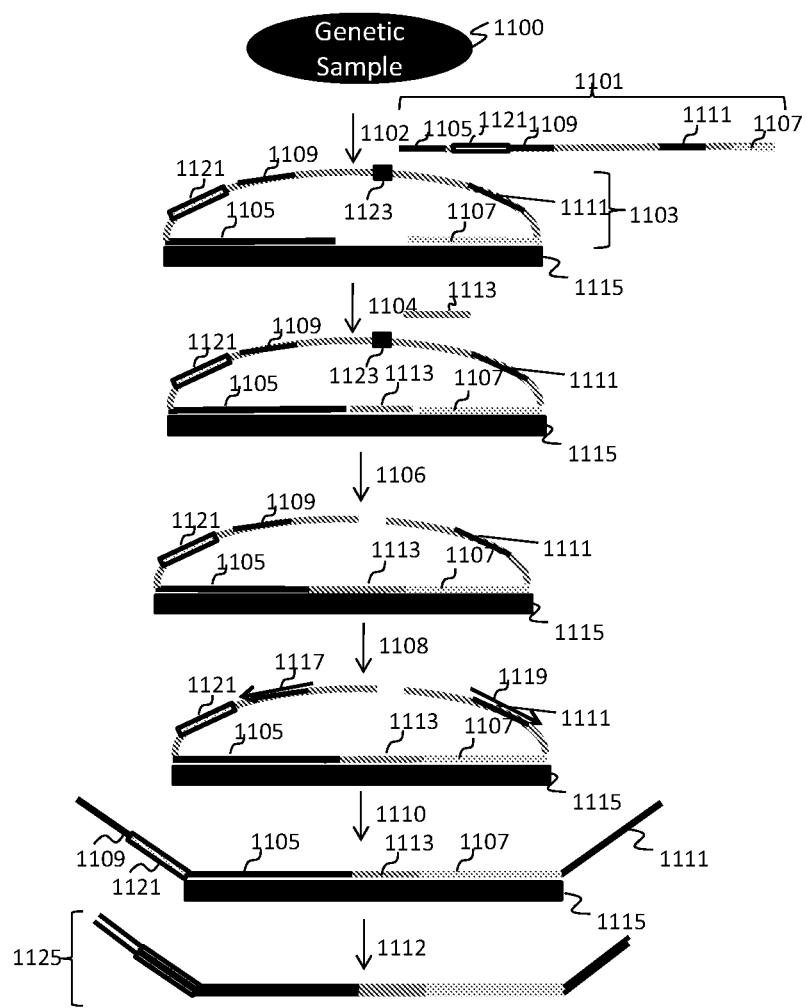
FIG. 11 illustrates an assay system utilizing a single fixed sequence oligonucleotide.

In specific aspects, such as the aspect illustrated in FIG. 11, the single fixed sequence oligonucleotide 1101 is complementary to the selected nucleic acid region 1115 on both ends. When this single fixed sequence oligonucleotide 1101 hybridizes to the selected nucleic acid region 1115, it forms a pre-circle oligonucleotide 1103 where the ends are separated by several nucleotides. The bridging oligonucleotide 1113 then binds between the complementary regions 1105, 1107 of the pre-circle oligonucleotide 1103 to fill this gap. The oligonucleotide regions 1105, 1107 of the pre-circle oligonucleotide 1103 bound to the genetic sample 1115 are then ligated together with the bridging oligonucleotide 1113, forming a complete circle.

The circular template is then preferably cleaved, and amplified using one or more of the universal primer sites. In specific aspects, a single universal primer region is used to replicate the template using techniques such as rolling circle replication, as disclosed in Lizardi et al., U.S. Pat. No. 6,558,928. In a preferred aspect, as illustrated in FIG. 11 this fixed sequence oligonucleotide has two universal priming sites 1109, 1111 on the circular template and optionally one or more indices 1121 between the ends that are complementary to the selected nucleic acid region. Preferably, a cleavage site 1123 exists between the two universal priming sites. Once circularized through ligation to the bridging oligo 1113, a nuclease can be used to remove all or most uncircularized oligonucleotides. After the removal of the uncircularized oligonucleotides, the circularized oligonucleotide is cleaved 1106, preserving and in some aspects exposing the universal priming sites 1109, 1111. Universal primers 1117, 1119 are added 1108 and a universal amplification occurs 1110 to create 1112 products 1125 that comprise the sequence of the nucleic acid region of interest. The products 1125 are detected and quantified through sequence determination of selected nucleic acid region or alternatively the index, which obviates the need for determining the actual sequences of the selected nucleic acid region. In other aspects, however, it is desirable to determine the product comprising sequences of both the index and the selected nucleic acid region, for example, to provide internal confirmation of the results or where the index provides sample information and is not informative of the selected nucleic acid region. As mentioned above, this single fixed sequence oligonucleotide methodology may be applied to any of the examples in FIGS. 1-10.

Resequencing

In a particular aspect, the assay system of the invention can be used to resequence a complex nucleic acid. The tandem ligation methods have been found to be exceptionally efficient, and this high efficiency allows the methodology to be expanded to the use of multiple oligos, preferably 2-100 or even more, that bind to nucleic acid regions of interest.

In the preferred aspect, the bridging oligos would be short, preferably between 1-10, more preferably between 2-7, even more preferably between 3-5 nucleotides in length, and the number of bridging oligos used in a tandem ligation reaction would be approximately 10-50. In a preferred aspect, the bridging oligos would be 5 bases in length and there would be approximately 15-30 ligations.

In one example, the bridging oligos might be selected to provide degeneracy for all possible sequence variants for the particular oligo length, for instance all sequence variations of 5-mers. Following the multiple ligations, one the ligated oligos can be amplified using the universal amplification techniques described herein, and sequence determination of the amplified products to identify the underlying sequence. This multiple ligation assay would provide the ability to target multiple sections of the genome simultaneously through universally amplification of tandem ligation products, and determination of their nucleotide composition.

Universal Amplification

In preferred aspects of the invention, universal amplification is used to amplify the ligation products created following hybridization of the fixed sequence oligonucleotides and the bridging oligonucleotides. In a multiplexed assay system, this is preferably done through universal amplification of the various nucleic acid regions to be analyzed using the assay systems of the invention. Universal primer sequences are added to the contiguous ligation products so that they may be amplified in a single universal amplification reaction. These universal primer sequences are preferably introduced in the fixed sequence oligonucleotides, although they may also be added to the proximal ends of the contiguous ligation products following ligation. The introduction of universal primer regions to the fixed sequence oligonucleotides allows a subsequent controlled universal amplification of all or a portion of selected nucleic acids prior to or during analysis, e.g. sequence determination.

Bias and variability can be introduced during DNA amplification, such as that seen during polymerase chain reaction (PCR). In cases where an amplification reaction is multiplexed, there is the potential that loci will amplify at different rates or efficiency. Part of this may be due to the variety of primers in a multiplex reaction with some having better efficiency (i.e. hybridization) than others, or some working better in specific experimental conditions due to the base composition. Each set of primers for a given locus may behave differently based on sequence context of the primer and template DNA, buffer conditions, and other conditions.

The whole tandem ligation reaction or an aliquot of the tandem ligation reaction may be used for the universal amplification. Using an aliquot allows different amplification reactions to be undertaken using the same or different conditions (e.g., polymerase, buffers, and the like), e.g., to ensure that bias is not inadvertently introduced due to experimental conditions. In addition, variations in primer concentrations may be used to effectively limit the number of sequence specific amplification cycles.

In certain aspects, the universal primer regions of the primers or adapters used in the assay system are designed to be compatible with conventional multiplexed assay methods that utilize general priming mechanisms to analyze large numbers of nucleic acids simultaneously. Such "universal" priming methods allow for efficient, high volume analysis of the quantity of nucleic acid regions present in a genetic sample, and allow for comprehensive quantification of the presence of nucleic acid regions within such a genetic sample for the determination of aneuploidy.

Examples of such assay methods include, but are not limited to, multiplexing methods used to amplify and/or genotype a variety of samples simultaneously, such as those described in Oliphant et al., U.S. Pat. No. 7,582,420.

Some aspects utilize coupled reactions for multiplex detection of nucleic acid sequences where oligonucleotides from an early phase of each process contain sequences which may be used by oligonucleotides from a later phase of the process. Exemplary processes for amplifying and/or detecting nucleic acids in samples can be used, alone or in combination, including but not limited to the methods described below, each of which are incorporated by reference in their entirety.

In certain aspects, the assay system of the invention utilizes one of the following combined selective and universal amplification techniques: (1) LDR coupled to PCR; (2) primary PCR coupled to secondary PCR coupled to LDR; and (3) primary PCR coupled to secondary PCR. Each of these aspects of the invention has particular applicability in detecting certain nucleic acid characteristics. However, each requires the use of coupled reactions for multiplex detection of nucleic acid sequence differences where oligonucleotides from an early phase of each process contain sequences which may be used by oligonucleotides from a later phase of the process.

Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe the use of the ligase detection reaction with detection reaction ("LDR") coupled with polymerase chain reaction ("PCR") for nucleic acid detection.

Barany et al., U.S. Pat. Nos. 7,556,924 and 6,858,412, describe the use of padlock probes (also called "precircle probes" or "multi-inversion probes") with coupled ligase detection reaction ("LDR") and polymerase chain reaction ("PCR") for nucleic acid detection.

Barany et al., U.S. Pat. Nos. 7,807,431, 7,709,201, and 7,198, 814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping, including Ronaghi et al., U.S. Pat. No. 7,622,281 describes amplification techniques for labeling and amplifying a nucleic acid using an adapter comprising a unique primer and a barcode.

In addition to the various amplification techniques, numerous methods of sequence determination are compatible with the assay systems of the inventions. Preferably, such methods include "next generation" methods of sequencing. Exemplary methods for sequence determination include, but are not limited to, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459, 311 and 6,210,891; Balasubramanian, U.S. Pat. Nos. 7,232, 656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Alternatively, nucleic acid regions of interest can be selected and/or identified using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al. Molecular Cloning: A Laboratory Manual ($2^{nd}$ Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386, 749, 6,391,623 each of which are incorporated herein by reference The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/

US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Use of Indices in the Assay Systems of the Invention

In certain aspects, all or a portion of the sequences of the nucleic acids of interest are directly detected using the described techniques, e.g., sequence determination or hybridization. In certain aspects, however, the nucleic acids of interest are associated with one or more indices that are identifying for a selected nucleic acid region or a particular sample being analyzed. The detection of the one or more indices can serve as a surrogate detection mechanism of the selected nucleic acid region, or as confirmation of the presence of a particular selected nucleic acid region if both the sequence of the index and the sequence of the nucleic acid region itself are determined. These indices are preferably associated with the selected nucleic acids during an amplification step using primers that comprise both the index and sequence regions that specifically hybridize to the nucleic acid region.

In one example, the primers used for amplification of a selected nucleic acid region are designed to provide a locus index between the selected nucleic acid region primer region and a universal amplification region. The locus index is unique for each selected nucleic acid region and representative of a locus on a chromosome of interest or reference chromosome, so that quantification of the locus index in a sample provides quantification data for the locus and the particular chromosome containing the locus.

In another example, the primers used for amplification of a selected nucleic acid region are designed to provide an allele index between the selected nucleic acid region primer region and a universal amplification region. The allele index is unique for particular alleles of a selected nucleic acid region and representative of a locus variation present on a chromosome of interest or reference chromosome, so that quantification of the allele index in a sample provides quantification data for the allele and the summation of the allelic indices for a particular locus provides quantification data for both the locus and the particular chromosome containing the locus.

In another aspect, the primers used for amplification of the selected nucleic acid regions to be analyzed for a genetic sample are designed to provide an identification index between the selected nucleic acid region primer region and a universal amplification region. In such an aspect, a sufficient number of identification indices are present to uniquely identify each selected nucleic acid region in the sample. Each nucleic acid region to be analyzed is associated with a unique identification index, so that the identification index is uniquely associated with the selected nucleic acid region. Quantification of the identification index in a sample provides quantification data for the associated selected nucleic acid region and the chromosome corresponding to the selected nucleic acid region. The identification locus may also be used to detect any amplification bias that occurs downstream of the initial isolation of the selected nucleic acid regions from a sample.

In certain aspects, only the locus index and/or the identification index (if present) are detected and used to quantify the selected nucleic acid regions in a sample. In another aspect, a count of the number of times each locus index occurs with a unique identification index is done to determine the relative frequency of a selected nucleic acid region in a sample.

In some aspects, indices representative of the sample from which a nucleic acid is isolated are used to identify the source of the nucleic acid in a multiplexed assay system. In such aspects, the nucleic acids are uniquely identified with the sample index. Those uniquely identified oligonucleotides may then be combined into a single reaction vessel with nucleic acids from other samples prior to sequencing. The sequencing data is first segregated by each unique sample index prior to determining the frequency of each target locus for each sample and prior to determining whether there is a chromosomal abnormality for each sample. For detection, the sample indices, the locus indices, and the identification indices (if present), are sequenced.

In aspects of the invention using indices, the fixed sequence oligonucleotides are preferably designed to comprise the indices. Alternatively, the indices and universal amplification sequences can be added to the selectively amplified nucleic acids following initial amplification. In either case, preferably the indices are encoded upstream of the nucleic acid region-specific sequences but downstream of the universal primers so that they are preserved upon amplification, but also require less sequencing to access when using the universal primers for sequence determination.

The indices are non-complementary but unique sequences used within the primer to provide information relevant to the selective nucleic acid region that is isolated and/or amplified using the primer. The advantage of this is that information on the presence and quantity of the selected nucleic acid region can be obtained without the need to determine the actual sequence itself, although in certain aspects it may be desirable to do so. Generally, however, the ability to identify and quantify a selected nucleic acid region through identification of one or more indices will decrease the length of sequencing required as the loci information is captured at the 3' or 5' end of the isolated selected nucleic acid region. Use of indices identification as a surrogate for identification of selected nucleic acid regions may also reduce error since longer sequencing reads are more prone to the introduction or error.

In addition to locus indices, allele indices and identification indices, additional indices can be introduced to primers to assist in the multiplexing of samples. For example, correction indices which identify experimental error (e.g., errors introduced during amplification or sequence determination) can be used to identify potential discrepancies in experimental procedures and/or detection methods in the assay systems. The order and placement of these indices, as well as the length of these indices, can vary, and they can be used in various combinations.

The primers used for identification and quantification of a selected nucleic acid region may be associated with regions complementary to the 5' of the selected nucleic acid region, regions complementary to the 5' of the selected nucleic acid region, or in certain amplification regimes the indices may be present on one or both of a set of amplification primers which comprise sequences complementary to the sequences of the selected nucleic acid region. The primers can be used to multiplex the analysis of multiple selected nucleic acid regions to be analyzed within a sample, and can be used either in solution or on a solid substrate, e.g., on a microarray or on a bead. These primers may be used for linear replication or amplification, or they may create circular constructs for further analysis.

Comparative Hybridization for Identification of Differential Frequency of Loci and Alleles In a specific aspect of the invention, an assay system of the invention employs two index sequences that allow direct comparison of levels of particular genomic regions in a sample using array hybridization. The assay employs directed analysis assays to select specific loci of interest using labeled oligonucleotides that selectively hybridize to two or more genomic regions within a sample. The oligonucleotides that selectively hybridize to different regions are differentially labeled so that the specific locus associated with a label can be identified. Preferably, the label is an optically detectable label (e.g., using a fluorescent label).

The first fixed oligonucleotide comprises sequences that selectively hybridize to a feature on the array (generally an oligonucleotide that is complementary to the first index) and a region that selectively hybridizes to a region of interest. The second fixed oligonucleotide comprises a region that selectively hybridizes to the same region of interest, either adjacently or within a selected number of intervening bases, and a region used to associate the oligonucleotide to the label. Where the fixed oligonucleotides bind to immediately adjacent regions on the array, the fixed oligonucleotides are ligated to create a contiguous ligation product comprising a locus- or allele-specific label that can be introduced to an array. In the case where the set of fixed oligonucleotides do not bind to immediately adjacent regions within the genomic region, the intervening region can be closed using primer extension, as discussed in previous sections, and/or one or more bridging oligonucleotides can be used that hybridize between the fixed sequence oligonucleotides. These are then ligated to create a contiguous ligation product with a locus- or allele-specific label.

Figure 12:
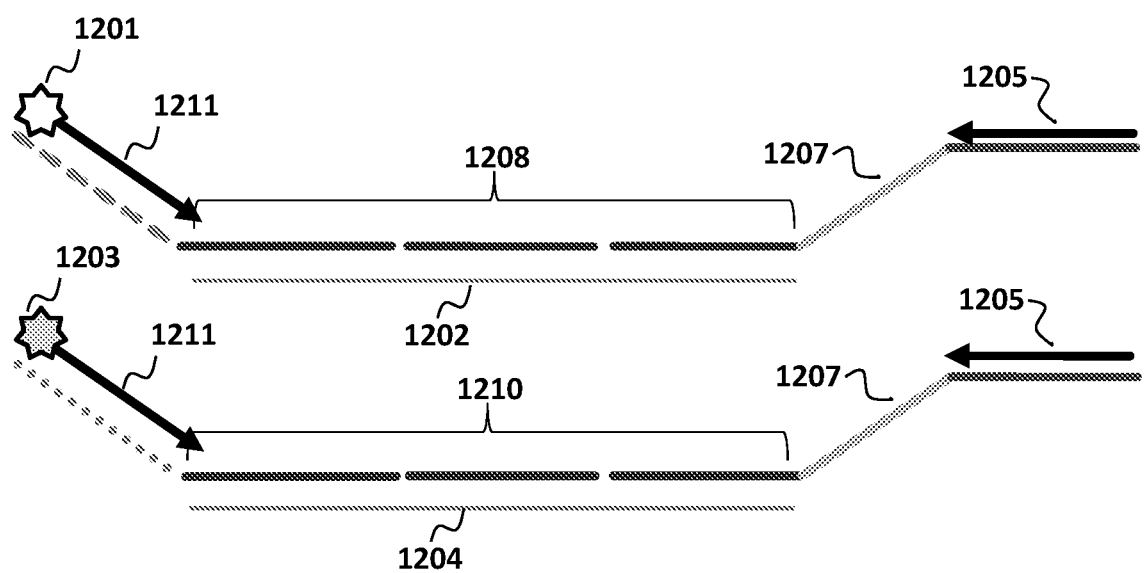
FIG. 12 illustrates a first comparative hybridization scheme using oligonucleotides that selectively hybridize to loci from two different chromosomes.

In one aspect, the sets of fixed sequence oligonucleotides are used in pairs, with each member of the pair selective for a different chromosome or locus. FIG. 12 Illustrates an example, where each set of the pair are selective for a genomic region on a different chromosome. Assay sets for two different chromosomes are evaluated competitively on a single hybridization feature on the array. Two fixed oligonucleotide sets 1208, 1210 selective for genomic regions 1202, 1204 on the two different chromosomes. Each set of fixed oligonucleotides is associated with an optically differentiated label 1201, 1203. Sequences complementary to universal primers 1205, 1211 are located at or near the ends of the fixed sequence oligonucleotides. Both of the contiguous ligation products created from the fixed oligonucleotides comprise sequences 1207 that are complementary to the same array feature. The level of hybridization of the optically differentiated contiguous ligation products can be measured to provide relative amount of the first chromosome region as compared to the second chromosome region.

Figure 13:
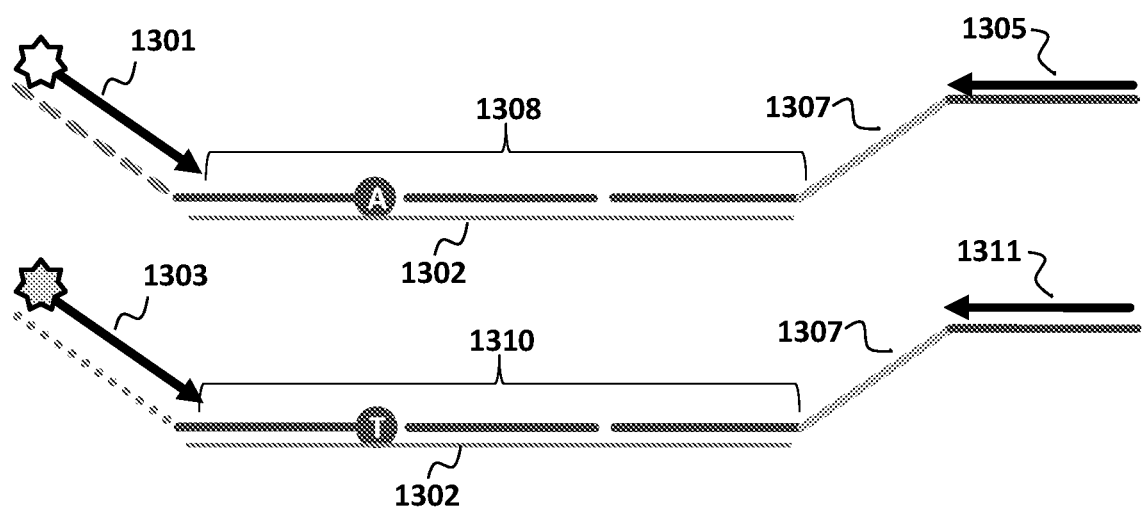
FIG. 13 illustrates a second comparative hybridization scheme using oligonucleotides that selectively hybridize to different alleles of a locus.

In another aspect, the sets of fixed sequence oligonucleotides are used in pairs, with each member of the pair selective for a different allele of a particular locus. FIG. 13 Illustrates such an example, where each set of the pair are selective for different alleles of the same locus. Assay sets for two different chromosomes are evaluated competitively on a single hybridization feature on the array. Two fixed oligonucleotide sets 1308, 1310 selective for a locus 1302 are used to create the contiguous ligation products. Each set of fixed oligonucleotides is associated with an optically differentiated label 1301, 1303. Sequences complementary to universal primers 1305, 1311 are located at or near the ends of the fixed sequence oligonucleotides. Both of the contiguous ligation products created from the fixed oligonucleotides comprise sequences 1307 that are complementary to the same array feature. The level of hybridization of the optically differentiated contiguous ligation products can be measured to provide relative amount of the first allele as compared to the second allele.

It will be apparent to those skilled in the art that various different regions can be used in such comparative hybridization assays, including sequences that are specific to different loci on a single chromosome, loci that are similar but polymorphic between chromosomes (e.g., loci on the pseudo-autosomal region of chromosomes X and Y) and the like.

In specific aspect, the detected levels of the contiguous hybridization products are normalized to reduce any assay-specific or technical variation in hybridization. The expected ratio of detection of the two labels for an assay pair and for many assay pairs from the same chromosomes are expected to be one if the regions are in the same relative abundance in a sample. A variance in the amount of one region (e.g., from a first chromosome) will cause a variance from the expected color ratio of one. A more abundant chromosome is expected to have the brighter color in the assay pair comparisons.

Detection of Other Agents or Risk Factors

Given the multiplexed nature of the assay systems of the invention, in certain aspects it may be beneficial to utilize the assay to detect other nucleic acids that could pose a risk to the health of the subject(s) or otherwise impact on clinical decisions about the treatment or prognostic outcome for a subject. Such nucleic acids could include but are not limited to indicators of disease or risk such as maternal alleles, polymorphisms, or somatic mutations known to present a risk for maternal or fetal health. Such indicators include, but are not limited to, genes associated with Rh status; mutations or polymorphisms associated with diseases such as diabetes, hyperlipidemia, hypercholesterolemia, blood disorders such as sickle cell anemia, hemophilia or thalassemia, cardiac conditions, etc.; exogenous nucleic acids associated with active or latent infections; somatic mutations or copy number variations associated with autoimmune disorders or malignancies (e.g., breast cancer), or any other health issue that may impact on the subject, and in particular on the clinical options that may be available in the treatment and/or prevention of health risks in a subject based on the outcome of the assay results.

Accordingly, as the preferred assay systems of the invention are highly multiplexed and able to interrogate hundreds or even thousands of nucleic acids within a mixed sample, in certain aspects it is desirable to interrogate the sample for nucleic acid markers within the mixed sample, e.g., nucleic acids associated with genetic risk or that identify the presence or absence of infectious organisms. Thus, in certain aspects, the assay systems provide detection of such nucleic acids in conjunction with the detection of nucleic acids for copy number determination within a mixed sample.

For example, in certain mixed samples of interest, including maternal samples, samples from subjects with autoimmune disease, and samples from patients undergoing chemotherapy, the immune suppression of the subject may increase the risk for the disease due to changes in the subject's immune system. Detection of exogenous agents in a mixed sample may be indicative of exposure to and infection by an infectious agent, and this finding have an impact on patient care or management of an infectious disease for which a subject tests positively for such infectious agent.

Specifically, changes in immunity and physiology during pregnancy may make pregnant women more susceptible to or more severely affected by infectious diseases. In fact, pregnancy itself may be a risk factor for acquiring certain infectious diseases, such as toxoplasmosis, Hansen disease, and listeriosis. In addition, for pregnant women or subjects with suppressed immune systems, certain infectious diseases such as influenza and varicella may have a more severe clinical course, increased complication rate, and higher case-fatality rate. Identification of infectious disease agents may therefore allow better treatment for maternal disease during pregnancy, leading to a better overall outcome for both mother and fetus.

In addition, certain infectious agents can be passed to the fetus via vertical transmission, i.e. spread of infections from mother to baby. These infections may occur while the fetus is still in the uterus, during labor and delivery, or after delivery (such as while breastfeeding).

Thus, is some preferred aspects, the assay system may include detection of exogenous sequences, e.g., sequences from infectious organisms that may have an adverse effect on the health and/or viability of the fetus or infant, in order to protect maternal, fetal, and or infant health.

Exemplary infections which can be spread via vertical transmission, and which can be tested for using the assay methods of the invention, include but are not limited to congenital infections, perinatal infections and postnatal infections.

Congenital infections are passed in utero by crossing the placenta to infect the fetus. Many infectious microbes can cause congenital infections, leading to problems in fetal development or even death. TORCH is an acronym for several of the more common congenital infections. These are: toxoplasmosis, other infections (e.g., syphilis, hepatitis B, Coxsackie virus, Epstein-Barr virus, varicella-zoster virus (chicken pox), and human parvovirus B19 (fifth disease)), rubella, cytomegalovirus (CMV), and herpes simplex virus.

Perinatal infections refer to infections that occur as the baby moves through an infected birth canal or through contamination with fecal matter during delivery. These infections can include, but are not limited to, sexually-transmitted diseases (e.g., gonorrhea, chlamydia, herpes simplex virus, human papilloma virus, etc.) CMV, and Group B Streptococci (GBS).

Infections spread from mother to baby following delivery are known as postnatal infections. These infections can be spread during breastfeeding through infectious microbes found in the mother's breast milk. Some examples of postnatal infections are CMV, Human immunodeficiency virus (HIV), Hepatitis C Virus (HCV), and GBS.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: General Aspects of the Assay Systems of the Invention

A number of assay formats were tested to demonstrate the ability to perform selective amplification and detection of independent loci to demonstrate multiplexed, ligation-based detection of a large number (e.g., 96 or more) of nucleic acid regions of interest using highly multiplexed formats.

These assays were designed based on human genomic sequences, and each interrogation consisted of two fixed sequence oligos per selected nucleic acid region interrogated in the assay. The first oligo, complementary to the 3' region of a genomic region, comprised the following sequential (5' to 3') oligo elements: a universal PCR priming sequence common to all assays: TACACCGGCGTTATGCGTCGA-GAC (SEQ ID NO:1); a nine nucleotide identification code specific to the selected loci; a 9 base locus- or locus/allele-specific sequence that acts as a locus code in the first SNP-independent set and a locus/allele code in the SNP-specific second set; a hybridization breaking nucleotide which is different from the corresponding base in the genomic locus; and a 20-24 bp sequence complementary to the selected genomic locus. In cases where a SNP is detected in this portion of the selected genomic locus, the allele-specific interrogation set consisted of two first tandem ligation primers, each with a different locus/allele code and a different allele-specific base at the SNP position. These first oligos were designed for each selected nucleic acid to provide a predicted uniform Tm with a two degree variation across all interrogations in the 480 assay set.

The second fixed sequence oligo, complementary to the 5' region of the genomic loci, comprised the following sequential (5' to 3') elements: a 20-24b sequence complementary to the 5' region in the genomic locus; a hybridization breaking nucleotide which was different from the corresponding base in the genomic locus; and a universal PCR priming sequence which was common to all third oligos in the assay set: ATTGCGGGGACCGATGATCGCGTC (SEQ ID NO:2). In cases where a SNP was detected in this portion of the selected genomic locus, the allele-specific interrogation set consisted of two tandem ligation primers, each with a different locus/allele code and a different allele-specific base at the SNP position. This second oligo was designed for each selected nucleic acid to provide a predicted uniform Tm with a two degree variation across all interrogations in the 480 assay set that was substantially the same Tm range as the first oligo set.

In certain tested aspects, one or more bridging oligos was used that were complementary to the genomic locus sequence between the region complementary to the first and second fixed sequence oligos used for each selected nucleic acid region. In specific aspects tested, more than one bridging oligo was used to span the gap between the fixed sequence oligonucleotides, and the one or more oligo may optionally be designed to identify one or more SNPs in the sequence. The length of the bridging oligonucleotides used in the assay systems varied from 5 to 36 base pairs.

All oligonucleotides used in the tandem ligation formats were synthesized using conventional solid-phase chemistry. The oligos of the first fixed set and the bridging oligonucleotides were synthesized with 5' phosphate moieties to enable ligation to 3' hydroxyl termini of adjacent oligonucleotides.

Example 2: Preparation of DNA for Use in Tandem Ligation Procedures

Genomic DNA from a Caucasian male (NA12801) or a Caucasian female (NA11995) was obtained from Coriell Cell Repositories (Camden, N.J.) and fragmented by acoustic shearing (Covaris, Woburn, Mass.) to a mean fragment size of approximately 200 bp.

The Coriell DNA was biotinylated using standard procedures. Briefly, the Covaris fragmented DNA was end-repaired by generating the following reaction in a 1.5 ml microtube: 5 ug DNA, ~12 µl 10× T4 ligase buffer (Enzymatics, Beverly Mass.), 50 U T4 polynucleotide kinase (Enzymatics, Beverly Mass.), and H2O to 120 µl. This was incubated at 37° C. for 30 minutes. The DNA was diluted using 10 mM Tris 1 mM EDTA pH 8.5 to desired final concentration of ~0.5 ng/ul.

5 µl DNA was placed in each well of a 96-well plate, and the plate sealed with an adhesive plate sealer and spun for 10 seconds at 250×g. The plate was then incubated at 95° C. for 3 minutes, and cooled to 25° C., and spun again for 10 seconds at 250×g. A biotinylation master mix was prepared in a 1.5 ml microtube to final concentration of: 1× TdT buffer (Enzymatics, Beverly Mass.), 8U TdT (Enzymatics, Beverly Mass.), 250 µM $CoCl_2$, 0.01 nmol/µl biotin-16-dUTP (Roche, Nutley N.J.), and $H_2O$ to 1.5 ml. 15 µl of the master mix was aliquoted into each well of a 96 well plate, and the plate sealed with adhesive plate sealer. The plate was spun for 10 seconds at 250×g and incubated for 37° C. for 60 minutes. Following incubation, the plate was spun again for 10 seconds at 250×g, and 7.5 µl precipitation mix (1 ng/µl Dextran Blue, 3 mM NaOAC) was added to each well.

The plate was sealed with an adhesive plate sealer and mixed using an IKA plate vortexer for 2 minutes at 3000 rpm. 27.5 µl of isopropanol was added into each well, the plate sealed with adhesive plate sealer, and vortexed for 5 minutes at 3000 rpm. The plate was spun for 20 minutes at 3000×g, the supernatant was decanted, and the plate inverted and centrifuged at 10×g for 1 minute onto an absorbent wipe. The plate was air-dried for 5 minutes, and the pellet resuspended in 10 µl 10 mM Tris pH8.0, 1 mM EDTA.

Example 3: Exemplary Assay Formats Using Tandem Ligation

Numerous tandem ligation assay formats using the biotinylated DNA were tested to illustrate proof of concept for the assay systems of the invention, and demonstrated the ability to perform highly multiplexed, targeted detection of a large number of independent loci using the series of different assay formats. The exemplary assay systems of the invention were designed to comprise 96 or more interrogations per loci in a genetic sample, and in cases where SNPs were detected the assay formats utilized 192 or more separate interrogations, each utilizing the detection of different alleles per 96 loci in genetic samples. The examples described for each assay format utilized two different sets of fixed sequence oligonucleotides and/or bridging oligos (as described in Example 1), comprising a total 96 or 192 interrogation reactions for the selected nucleic acid regions depending upon whether SNPs were identified.

A first exemplary assay format used locus-specific fixed sequence oligos and bridging oligos, where there was a one base gap between the first fixed sequence oligo and the bridging oligos, and a second one base gap between the bridging oligos and the second fixed sequence oligo, Each of the two gaps encompassed two different SNPs. In this format, a DNA polymerase was used to incorporate each of the SNP bases, and ligase was used to seal the nicks formed thereby. SNP base discrimination derived from the fidelity of base incorporation by the polymerase, and in the event of mis-incorporation, the tendency of ligase to not seal nicks adjacent to mismatched bases.

The second exemplary assay format used two locus-specific fixed sequence oligonucleotides without a bridging oligo, where there was a ~15-35 base gap between the fixed sequence oligos, and where the gap spanned one or more SNPs. In this format, a polymerase was used to incorporate the missing bases, and a ligase was used to seal the nick formed thereby. SNP base discrimination derived from the fidelity of base incorporation by the polymerase, and in the event of misincorporation, the tendency of ligase to not seal nicks adjacent to mismatched bases.

A third exemplary assay format used allele-specific first and second fixed sequence oligos without a bridging oligo, where there was a ~15-35 base gap between the first and second fixed sequence oligos, and where the gap spanned one or more SNPs. Two separate allele-specific first fixed sequence oligos and two separate allele-specific second fixed sequence oligos were used. A polymerase was used to incorporate the missing bases, and a ligase was used to seal the nick formed thereby. SNP base discrimination derived from hybridization specificity, the tendency of non-proofreading polymerase to not extend annealed primers with mismatches near the 3' end, and the tendency of the ligase to not seal nicks adjacent to mismatched bases.

A fourth exemplary format used allele-specific fixed sequence oligos and a locus-specific bridging oligo. In this format, two separate fixed sequence oligos complementary to the 3'end of the loci of interest, the first with a 3' base specific for one allele of the targeted SNP, and the second with a 3' base specific for the other allele of the targeted SNP. Similarly, two separate second fixed sequence oligos were used, the first with a 5' base specific for one allele of a second targeted SNP, and the second with a 5' base specific for the other allele of the second targeted SNP. The bridging oligos were complementary to the region directly adjacent to the locus regions complementary to the first and second fixed sequence oligos, and thus no polymerase was needed prior to ligation. Ligase was used to seal the nicks between the fixed sequence oligos and the bridging oligo. SNP base discrimination in this assay format derived from hybridization specificity and the tendency of the ligase to not seal nicks adjacent to mismatched bases. This exemplary format was tested using either T4 ligase or Taq ligase for creation of the contiguous template, and both were proved effective in the reaction as described below.

A fifth exemplary format used locus-specific fixed sequence oligos that were complementary to adjacent regions on the nucleic acid of interest, and thus no gap was created by hybridization of these oligos. In this format, no polymerase was required, and a ligase was used to seal the single nick between the oligos.

A sixth exemplary format used allele-specific fixed sequence oligos and locus-specific bridging oligos, where there was a short base gap of five bases between the loci region complementary to the fixed sequence oligos. The locus-specific bridging oligo in this example was a 5mer complementary to the regions directly adjacent to the regions complementary to the first and second fixed sequence oligos. In this format, no polymerase was required, and a ligase was used to seal the two nicks between the oligos.

A seventh exemplary format used locus-specific fixed sequence oligos and a locus-specific bridging oligo, where there was a shorter base gap of five bases containing a SNP in the region complementary to the bridging oligo. Allele-specific bridging oligos corresponding to the possible SNPs were included in the hybridization and ligation reaction. In this format, no polymerase was required, and a ligase is used to seal the two nicks between the oligos. SNP base discrimination in this assay format derives from hybridization specificity and the tendency of the ligase to not seal nicks adjacent to mismatched bases.

An eighth exemplary format used locus-specific fixed sequence oligos and two adjacent locus-specific bridging oligos, where there is a 10 base gap between the regions complementary to the first and second fixed sequence oligos. Locus-specific bridging oligos were included in the ligation reaction, with the gap requiring two contiguous 5mers to bridge the gap. In this format, no polymerase is required, and a ligase is used to seal the three nicks between the oligos.

For each of the above-described assay formats, an equimolar pool (40 nM each) of sets of first and second loci- or allele-specific fixed oligonucleotides was created from the oligos prepared as set forth in Example 2. A separate equimolar pool (20 µM each) of bridging oligonucleotides was likewise created for the assay processes based on the sequences of the selected genomic loci.

10 µg of strepavidin beads were transferred into the wells of a 96 well plate, and the supernatant was removed. 60 µl BB2 buffer (100 mM Tris pH 8.0, 10 mM EDTA, 500 mM NaCl2, 58% formamide, 0.17% Tween-80), 10 µL 40 nM fixed sequence oligo pool and 30 µL of the biotinylated template DNA prepared in Example 2 were added to the beads. The plate was sealed with an adhesive plate sealer and vortexed at 3000 rpm until beads were resuspended. The oligos were annealed to the template DNA by incubation at 70 C for 5 minutes, followed by slow cooling to room temperature.

The plate was placed on a raised bar magnetic plate for 2 minutes to pull the magnetic beads and associated DNA to the side of the wells. The supernatant was removed by pipetting, and was replaced with 50 uL of 60% BB2 (v/v in water). The beads were resuspended by vortexing, placed on the magnet again, and the supernatant was removed. This bead wash procedure was repeated once using 50 uL 60% BB2, and repeated twice more using 50 uL wash buffer (10 mM Tris pH 8.0, 1 mM EDTA, 50 mM NaCl2).

The beads were resuspended in 37 µl ligation reaction mix consisting of 1× Taq ligase buffer (Enzymatics, Beverly Mass.), 10U Taq ligase, and 2 uM bridging oligo pool (depending on the assay format), and incubated at 37° C. for one hour. Where appropriate, and depending on the assay format, a non-proofreading thermostable polymerase plus 200 nM each dNTP was included in this mixture. The plate was placed on a raised bar magnetic plate for 2 minutes to pull the magnetic beads and associated DNA to the side of the wells. The supernatant was removed by pipetting, and was replaced with 50 uL wash buffer. The beads were resuspended by vortexing, placed on the magnet again, and the supernatant was removed. The wash procedure was repeated once.

To elute the products from the strepavidin beads, 30 µl of 10 mM Tris 1 mM EDTA, pH 8.0 was added to each well of 96-well plate. The plate was sealed and mixed using an IKA vortexer for 2 minutes at 3000 rpm to resuspend the beads. The plate was incubated at 95° C. for 1 minute, and the supernatant aspirated using an 8-channel pipetter. 25 µl of supernatant from each well was transferred into a fresh 96-well plate for universal amplification.

Example 4: Universal Amplification of Tandem Ligated Products

The polymerized and/or ligated nucleic acids were amplified using universal PCR primers complementary to the universal sequences present in the first and second fixed sequence oligos hybridized to the nucleic acid regions of interest. 25 µl of each of the reaction mixtures of Example 3 were used in each amplification reaction. A 50 uL universal PCR reaction consisting of 25 uL eluted ligation product plus 1× Pfusion buffer (Finnzymes, Finland), 1M Betaine, 400 nM each dNTP, 1 U Pfusion error-correcting thermostable DNA polymerase, and the following primer pairs:
TAATGATACGGCGACCACCGAGATCTA-CACCGGCGTTATGCGT CGAGA (SEQ ID NO:3) and
TCAAGCAGAAGACGGCAT-ACGAGATXAAACGACGCGATCATCG GTCCCCGCAA (SEQ ID NO:4), where X represents one of 96 different sample tags used to uniquely identify individual samples prior to pooling and sequencing. The PCR was carried out under stringent conditions using a BioRad Tetrad™ thermocycler.

10 µl of universal PCR product from each of the samples were pooled and the pooled PCR product was purified using AMPure™ SPRI beads (Beckman-Coulter, Danvers, Mass.), and quantified using Quant-iT™ PicoGreen, (Invitrogen, Carlsbad, Calif.).

Example 5: Detection and Analysis of Selected Loci

The purified PCR products of each assay format were sequenced on a single lane of a slide on an Illumina HiSeq 2000. Sequencing runs typically give rise to ~100M raw reads, of which ~85M (85%) mapp to expected assay structures. This translat to an average of ~885K reads/sample across the experiment, and (in the case of an experiment using 96 loci) 9.2K reads/replicate/locus across 96 loci. The mapped reads were parsed into replicate/locus/allele counts, and various metrics were computed for each condition, including:

Yield: a metric of the proportion of input DNA that was queried in sequencing, computed as the average number of unique reads per locus (only counting unique identification code reads per replicate/locus) divided by the total number of genomic equivalents contained in the input DNA.

80 percentile locus frequency range: a metric of the locus frequency variability in the sequencing data, interpreted as the fold range that encompasses 80% of the loci. It is computed on the distribution of total reads per locus, across all loci, as the 90th percentile of total reads per locus divided by the 10th percentile of the total reads per locus.

SNP error rate: a metric of the error rate at the SNP position, and computed as the proportion of reads containing a discordant base at the SNP position.

These results are summarized in Table 1:

TABLE 1

Results Summary of Tandem Ligation Assay Formats

| ASSAY FORMAT | FIXED SEQUENCE OLIGO (1st and/or 2nd) | BRIDGING OLIGO USED | ENZYME USED | YIELD | 80% LOC FREQ RANGE | SNP ERROR RATE |
|---|---|---|---|---|---|---|
| 1 | LOCUS-SPECIFIC | Locus specific | pol + lig | 9.5% | 5.3 | 0.18% |
| 2 | LOCUS-SPECIFIC | No | pol + lig | 1.4% | 58.3 | 0.19% |
| 3 | ALLELE-SPECIFIC | No | pol + lig | 0.4% | 61.7 | 1.00% |
| 4 | ALLELE-SPECIFIC | Locus specific | Taq lig | 5.0% | 5.9 | 0.92% |
| 4 | ALLELE-SPECIFIC | Locus specific | T4 lig | 5.3% | 4.4 | 0.95% |
| 5 | LOCUS-SPECIFIC | No | Taq lig | 22.5% | 1.7 | NA |
| 6 | LOCUS-SPECIFIC | Locus specific | Taq lig | 12.5 | 2.9 | NA |
| 7 | LOCUS-SPECIFIC | Allele specific | Taq lig | 14.3 | 2.8 | 0.20% |
| 8 | LOCUS-SPECIFIC | 2 Locus specific | Taq lig | 18.5% | 2.8 | NA |

Table 1 indicates that the locus-specific tandem ligation assay using a bridging oligo converted template DNA into targeted product with high yield (~10%), with a high proportion of product derived from targeted loci (15% of reads did not contain expected assay structures), with limited locus bias (80% of loci fall within a ~5-fold concentration range), and with high SNP accuracy (0.2% SNP error rate). The locus-specific tandem ligation assay without the use of a bridging oligo produced reduced yields and substantial locus bias, but still produced high accuracy SNP genotyping data. The allele-specific tandem ligation assay with a bridging oligo produced intermediate yields compared to the locus-specific assay using both T4 and Taq ligase, but still produced limited locus bias and high accuracy SNP genotyping data. The allele-specific tandem ligation assay without a bridging produced reduced yields and substantial locus bias, but still produced high accuracy SNP genotyping data.

Figure 14:
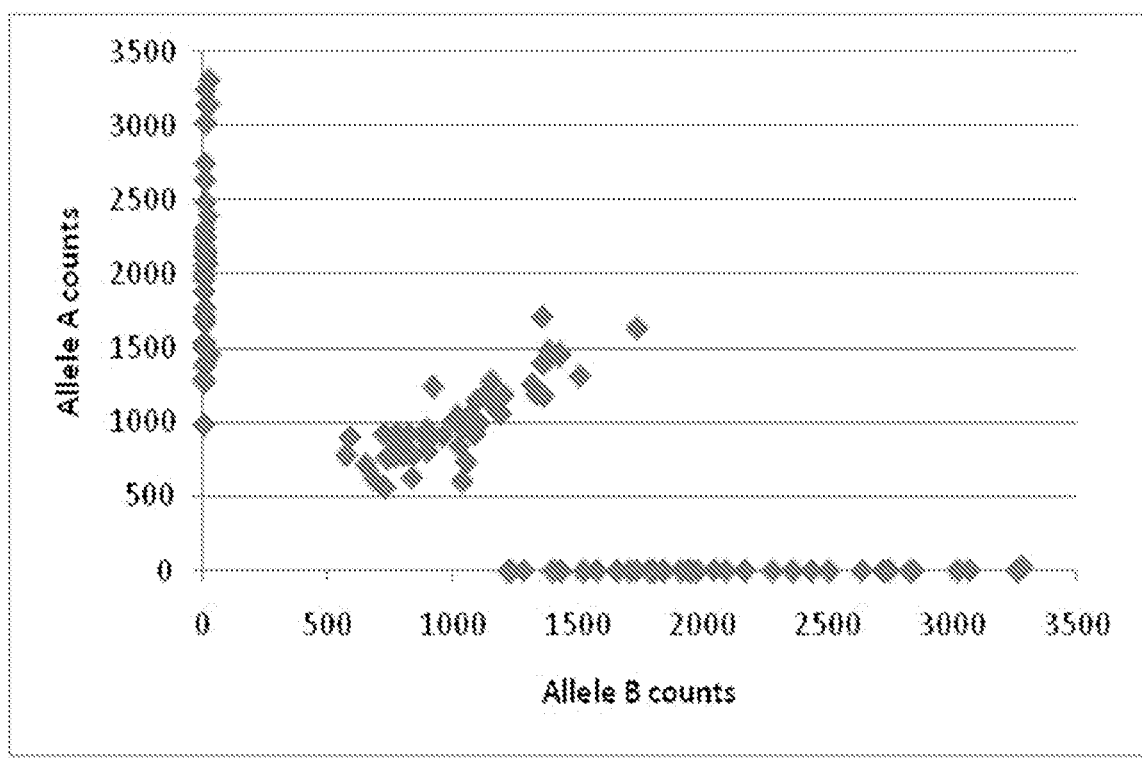
FIG. 14 illustrates the genotyping performance that is obtained using one exemplary assay format.

Assay formats five and six showed that template DNA can be converted into targeted product with high yield (12-16%), with a high proportion of product derived from targeted loci (~76% of reads contained expected assay structures), and with limited locus bias (80% of loci fall within a 2-3-fold concentration range). FIG. 14 illustrates the genotyping performance that is obtained using assay format seven, comparing the sequence counts for the two alleles of all polymorphic assays observed in a single sample. Note the clear separation of the homozygous and heterozygous clusters, as well as the low background counts observed amongst the homozygous clusters.

Example 6: Determination of Percent Fetal DNA Using Tandem Ligation

One exemplary assay system of the invention was designed comprising 480 separate interrogations, each utilizing the detection of different loci in a maternal sample. The initial example utilized a determination of percent fetal DNA in subjects carrying a male fetus, and so loci on the Y chromosome were utilized as well as loci containing a paternally-inherited fetal SNP that is different from the maternal sequence.

Specifically, 480 selected nucleic acids were interrogated using the assay system. The 480 selected nucleic acids comprised 48 sequence-specific interrogations of nucleic acids corresponding to loci on chromosome Y, 192 sequence-specific interrogations of nucleic acids corresponding to loci on chromosome 21, 192 sequence-specific interrogations of selected nucleic acids corresponding to loci on chromosome 18, and 144 sequence-specific interrogations of selected nucleic acids corresponding to polymorphic loci on chromosomes 1-16 which. These assays were designed based on human genomic sequences, and each interrogation used three oligos per selected nucleic acid interrogated in the assay.

The first oligo used for each interrogation was complementary to the 3' region of the selected genomic region, and comprised the following sequential (5' to 3') oligo elements: a universal PCR priming sequence common to all assays: TACACCGGCGTTATGCGTCGAGAC (SEQ ID NO:1); an identification code specific to the selected loci comprising nine nucleotides; and a 20-24 bp sequence complementary to the selected genomic locus. This first oligo was designed for each selected nucleic acid to provide a predicted uniform Tm with a two degree variation across all interrogations in the 480 assay set.

The second oligo used for each interrogation was a bridging oligo complementary to the genomic locus sequence directly adjacent to the genomic region complementary to the first oligonucleotide. Based on the selected nucleic acids of interest, the bridging oligos were designed to allow utilization of a total of 12 oligonucleotide sequences that could serve as bridging oligos for all of the 480 interrogations in the assay set.

The third oligo used for each interrogation was complementary to the 5' region of the selected genomic locus, comprised the following sequential (5' to 3') elements: a 20-24b sequence complimentary to the 5' region in the genomic locus; a hybridization breaking nucleotide which was different from the corresponding base in the genomic locus; and a universal PCR priming sequence which is common to all third oligos in the assay set: ATTGCGGGGACCGATGATCGCGTC (SEQ ID NO:2). This third oligo was designed for each selected nucleic acid to provide a predicted uniform Tm with a two degree variation across all interrogations in the 480 assay set, and the Tm range was substantially the same as the Tm range as the first oligo set.

All oligonucleotides were synthesized using conventional solid-phase chemistry. The first and bridging oligonucleotides were synthesized with 5' phosphate moieties to enable ligation to 3' hydroxyl termini of adjacent oligonucleotides. An equimolar pool of sets of the first and third oligonucleotides used for all interrogations in the multiplexed assay was created, and a separate equimolar pool of all bridging oligonucleotides was created to allow for separate hybridization reactions.

Genomic DNA was isolated from 5 mL plasma using the Dynal Silane viral NA kit (Invitrogen, Carlsbad, Calif.). Approximately 12 ng DNA was processed from each of 37 females, including 7 non-pregnant female subjects, 10 female subjects pregnant with males, and 22 female subjects pregnant with females. The DNA was biotinylated using standard procedures, and the biotinylated DNA was immobilized on a solid surface coated with strepavidin to allow retention of the genomic DNA in subsequent assay steps.

The immobilized DNA was hybridized to the first pool comprising the first and third oligos for each interrogated sequences under stringent hybridization conditions. The unhybridized oligos in the pool were then washed from the surface of the solid support, and the immobilized DNA was hybridized to the pool comprising the bridging oligonucleotides under stringent hybridization conditions. Once the bridging oligonucleotides were allow to hybridize to the immobilized DNA, the remaining unbound oligos were washed from the surface and the three hybridized oligos bound to the selected nucleic acid regions were ligated using T4 ligase to provide a contiguous DNA template for amplification.

The ligated DNA was amplified from the solid substrate using an error correcting thermostable DNA polymerase, a first universal PCR primer TAATGATACGGCGAC-CACCGAGATCTACACCGGCGTTATGCGTCGAGA (SEQ ID NO:3) and a second universal PCR primer TCAAGCAGAAGACGGCAT-ACGAGATXAAACGACGCGATCATCGGTCCCC GCAA (SEQ ID NO:4), where X represents one of 96 different sample indices used to uniquely identify individual samples prior to pooling and sequencing. 10 µL of universal PCR product from each of the 37 samples described above were and the pooled PCR product was purified using AMPure SPRI beads (Beckman-Coulter, Danvers, Mass.), and quantified using Quant-iT™ PicoGreen, (Invitrogen, Carlsbad, Calif.).

The purified PCR product was sequenced on 6 lanes of a single slide on an Illumina HiSeg™ 2000. The sequencing run gave rise to 384M raw reads, of which 343M (89%) mapped to expected genomic loci, resulting in an average of 3.8M reads per sample across the 37 samples, and 8K reads per sample per locus across the 480 loci. The mapped reads were parsed into sample and locus counts, and two separate metrics of percent fetal DNA were computed as follows.

Percent male DNA detected by chromosome Y loci corresponds to the relative proportion of reads derived from chromosome Y locus interrogations versus the relative proportion of reads derived from autosomal locus interrogations, and is computed as (number of chromosome Y reads in a test subject/number of autosome reads in test subject)/ (number of reads in male control subject/number of autosome reads in the male control subject). This metric was used as a measure of percent fetal DNA in the case of a male fetus using the relative reads of chromosome Y.

Percent fetal DNA detected by polymorphic loci corresponds to the proportion of reads derived from non-maternal versus maternal alleles at loci where such a distinction can be made. First, for each identified locus, the number of reads for the allele with the fewest counts (the low frequency allele) was divided by the total number of reads to provide a minor allele frequency (MAF) for each locus. Then, loci with an MAF between 0.075% and 15% were identified as informative loci. The estimated percent fetal DNA for the sample was calculated as the mean of the minor allele frequency of the informative loci multiplied by two, i.e. computed as 2× average (MAF) occurrence where 0.075%<MAF<15%.

Figure 15:
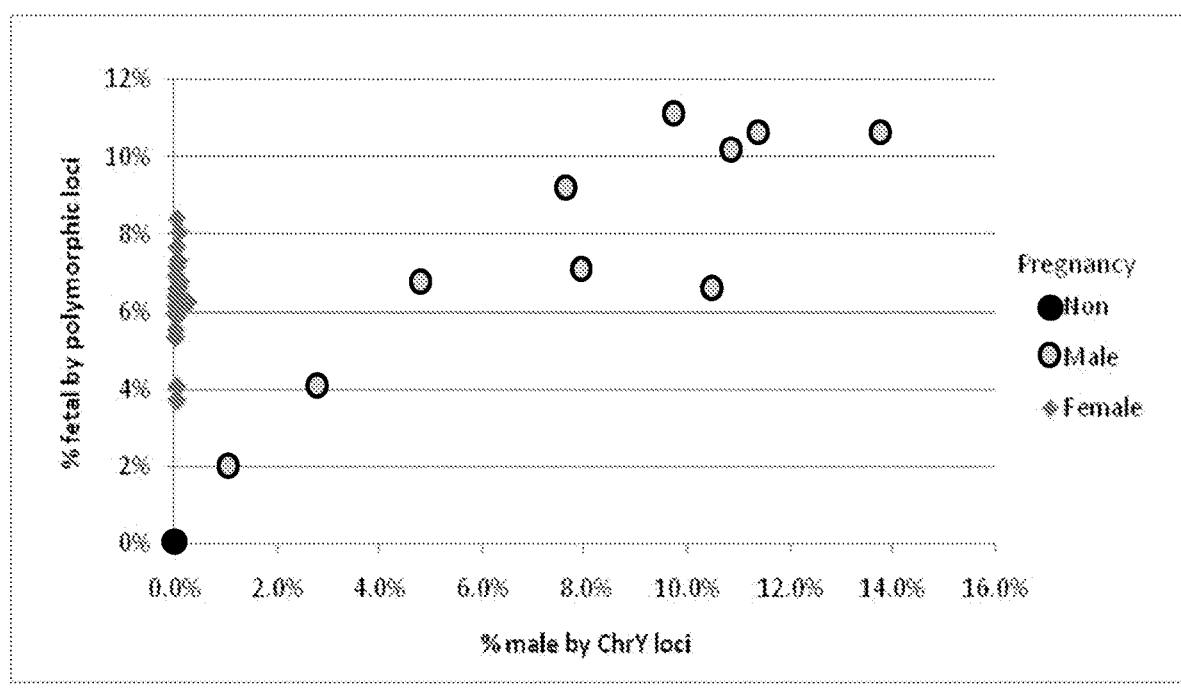
FIG. 15 is a graph illustrating the ability of the assay system to determine percent fetal DNA in a maternal sample.

FIG. 15 demonstrates the results from these computations. As shown in FIG. 15, the percent male loci determined using the above-described chromosome Y metrics (grey circles) can separate pregnancies involving male fetuses from pregnancies involving female fetuses (grey diamonds) and non-pregnant samples (black circles). In addition, computation of the percent fetal amount in a sample by polymorphic loci metric can distinguish pregnant samples from non-pregnant samples. Finally, there is a correlation between the percent fetal DNA estimates for a sample obtained from chromosome Y and polymorphic loci in pregnancies involving male fetuses. This correlation persists down to quite low percent fetal values.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A method for detecting a fetal copy number variation (CNV) in a maternal plasma or serum sample comprising maternal and fetal cell-free DNA, comprising the steps of:
   (a) introducing at least 48 first sets of first and second fixed sequence oligonucleotides to the cell-free DNA from the maternal plasma or serum sample under conditions that allow the first sets of fixed sequence oligonucleotides to specifically hybridize to non-polymorphic loci in a first genomic region of interest, wherein:
      (i) at least one fixed sequence oligonucleotide in each first set comprises at first label and a binding region that binds selectively to an array feature, wherein the binding region in each first set is different from the binding regions in each other first set,
      (ii) the first and second fixed sequence oligonucleotides in each first set hybridize directly adjacent to each other or are separated by a gap of one or more nucleotides, and
      (iii) wherein melting temperatures ($T_m$s) of first fixed sequence oligonucleotides of each first set of first and second fixed sequence oligonucleotides vary in a range of two degrees centigrade;
   (b) introducing at least 48 second sets of first and second fixed sequence oligonucleotides to the cell-free DNA from the maternal plasma or serum sample under conditions that allow the second sets of fixed sequence oligonucleotides to specifically hybridize to non-polymorphic loci in a second genomic region of interest, wherein:
      (i) at least one fixed sequence oligonucleotide in each second set comprises a second label and binding region that binds selectively to an array feature, wherein the binding region in each second set is different from the binding regions in each other second set, and wherein the binding region in each second set is the same as the binding region in one first set and binds to the same array feature,
      (ii) the first and second fixed sequence oligonucleotides in each second set hybridize directly adjacent to each other or are separated by a gap of one or more nucleotides, and
      (iii) wherein melting temperatures ($T_m$s) of first fixed sequence oligonucleotides of each second set of first and second fixed sequence oligonucleotides vary in a range of two degrees centigrade;
   (c) hybridizing the first and second sets of fixed sequence oligonucleotides to the cell-free DNA from the maternal plasma or serum sample;
   (d) if the first and second fixed sequence oligonucleotides of each first and second set are separated by a gap of one or more nucleotides,
      (i) hybridizing bridging oligonucleotides with the cell-free DNA from the maternal plasma or serum sample, wherein the bridging oligonucleotides are complementary to regions in the loci between the first and second fixed sequence oligonucleotides of each first and second set, to create adjacently hybridized oligonucleotides, or
  (ii) extending the hybridized fixed sequence oligonucleotides with a polymerase to create adjacently hybridized oligonucleotides;
(e) ligating the hybridized fixed sequence oligonucleotides to create contiguous ligation products complementary to the non-polymorphic loci in the first and second genomic regions of interest;
(f) introducing the contiguous ligation products to an array comprising array features complementary to binding regions in the contiguous ligation products;
(g) detecting hybridization of the contiguous ligation products from the first and second sets of fixed sequence oligonucleotides to the array by detection of the first and second labels at each array feature;
(h) determining frequencies of the first and second genomic regions of interest based on the detected levels of the first and second labels; and
(i) detecting a fetal CNV based on the frequencies of the first and second genomic regions of interest.

2. The method of claim 1, further comprising amplifying the contiguous ligation products prior to introduction to the array.

3. The method of claim 2, wherein at least one of the first or second fixed sequence oligonucleotides of each first and second set comprise universal primer regions.

4. The method of claim 1, wherein the hybridization products of the fixed sequence oligonucleotides and the non-polymorphic loci of interest to which they hybridize are isolated prior to introduction of the bridging oligonucleotides.

5. The method of claim 1, wherein the one or more bridging oligonucleotides are introduced simultaneously with the fixed sequence oligonucleotides.

6. The method of claim 1, wherein the first and second labels are fluorescent labels.

7. The method of claim 1, wherein the method is carried out for at least 100 first sets of fixed sequence oligonucleotides complementary to non-polymorphic loci on the first chromosome and at least 100 second sets of fixed sequence oligonucleotides complementary non-polymorphic loci on the second chromosome.

8. The method of claim 1, wherein the method is carried out for at least 200 first sets of fixed sequence oligonucleotides complementary to non-polymorphic loci on the first chromosome and at least 200 second sets of fixed sequence oligonucleotides complementary non-polymorphic loci on the second chromosome.

9. The method of claim 1, wherein the method is carried out for at least 500 first sets of fixed sequence oligonucleotides complementary to non-polymorphic loci on the first chromosome and at least 500 second sets of fixed sequence oligonucleotides complementary non-polymorphic loci on the second chromosome.

10. The method of claim 1, wherein unhybridized fixed sequence oligonucleotides are removed prior to introduction of the bridging oligonucleotides.

11. The method of claim 1, wherein the first or second fixed sequence oligonucleotide of each first and second set comprises a sample index.

12. The method of claim 1, wherein the first or second fixed sequence oligonucleotide of each first and second set comprises a locus index.

13. The method of claim 1, wherein the first and second genomic regions of interest are chromosomes.

14. The method of claim 13, wherein the chromosome is selected from the group consisting of: chromosome 13, chromosome 18, chromosome 21, the X chromosome, and the Y chromosome.

15. The method of claim 1, wherein the copy number variation is selected from the group consisting of a deletion, a duplication, a rearrangement, and a translocation.

16. The method of claim 1, further comprising determination of percent fetal DNA in the maternal plasma or serum sample.

* * * * *